(12) United States Patent
Adachi et al.

(10) Patent No.: US 11,371,975 B2
(45) Date of Patent: Jun. 28, 2022

(54) GAS SENSOR AND PROTECTIVE COVER

(71) Applicant: NGK INSULATORS, LTD., Aichi (JP)

(72) Inventors: Yosuke Adachi, Nagoya (JP); Takeshi Omori, Niwa-gun (JP)

(73) Assignee: NGK INSULATORS, LTD., Nagoya (JP)

(*) Notice: Subject to any disclaimer, the term of this patent is extended or adjusted under 35 U.S.C. 154(b) by 87 days.

(21) Appl. No.: 17/038,099

(22) Filed: Sep. 30, 2020

(65) Prior Publication Data
US 2021/0102926 A1    Apr. 8, 2021

(30) Foreign Application Priority Data

Oct. 3, 2019   (JP) .............................. JP2019-183072
Jul. 28, 2020   (JP) .............................. JP2020-127253

(51) Int. Cl.
*G01N 33/00*    (2006.01)
*G01N 27/407*    (2006.01)

(52) U.S. Cl.
CPC ..... *G01N 33/0009* (2013.01); *G01N 27/4077* (2013.01)

(58) Field of Classification Search
CPC ...................... G01N 33/0009; G01N 27/4077
USPC ...................... 73/31.05, 23.2, 232
See application file for complete search history.

(56) References Cited

U.S. PATENT DOCUMENTS

| | | | |
|---|---|---|---|
| 9,952,072 B2* | 4/2018 | Murakami | G01D 11/245 |
| 2003/0177813 A1* | 9/2003 | Sakamoto | G01N 29/222 |
| | | | 73/24.01 |
| 2008/0156644 A1 | 7/2008 | Suzuki et al. | |
| 2016/0153814 A1* | 6/2016 | Seimori | G01N 33/0054 |
| | | | 73/431 |
| 2016/0252372 A1* | 9/2016 | Rentschler | G01M 15/102 |
| | | | 73/431 |
| 2017/0363596 A1 | 12/2017 | Adachi et al. | |

FOREIGN PATENT DOCUMENTS

| | | |
|---|---|---|
| JP | 2008-164411 A | 7/2008 |
| JP | 2017-223620 A | 12/2017 |

OTHER PUBLICATIONS

Unexamined U.S. Appl. No. 17/038,103, filed Sep. 30, 2020.
Unexamined U.S. Appl. No. 17/038,109, filed Sep. 30, 2020.
Unexamined U.S. Appl. No. 17/038,110, filed Sep. 30, 2020.

* cited by examiner

*Primary Examiner* — Nimeshkumar D Patel
*Assistant Examiner* — Jean F Morello
(74) *Attorney, Agent, or Firm* — Mattingly & Malur, PC

(57) ABSTRACT

A gas sensor includes a sensor element, an inner protective cover having one or more element chamber inlets and including a first member and a second member, and an outer protective cover having one or more outer inlets. A first gas chamber between the outer protective cover and the inner protective cover has a first space and a second space. A cross-sectional area Cs that is a flow channel cross-sectional area in the second space when the measurement-object gas passes from an outside of the second member toward an inside of the second member just above the second member is greater than or equal to 14.0 mm$^2$, and a cross-sectional area Ds that is a cross-sectional area perpendicular to a circumferential direction of the inner protective cover in the second space is greater than or equal to 0.5 mm$^2$ and less than or equal to 6.4 mm$^2$.

9 Claims, 10 Drawing Sheets

[Fig. 1]
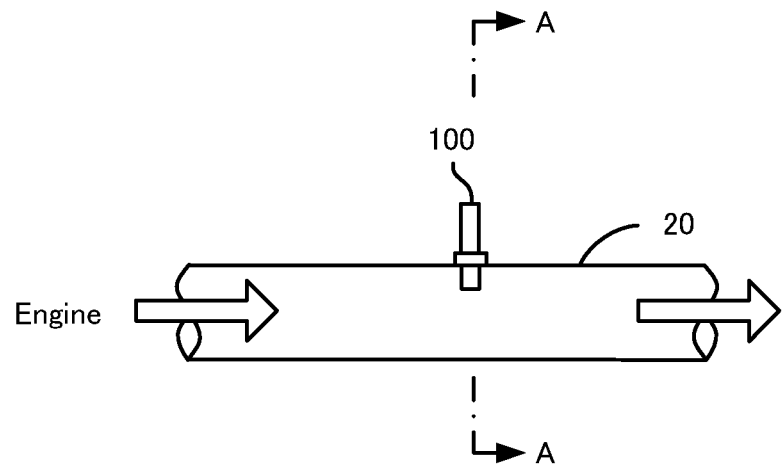
[Fig. 2]
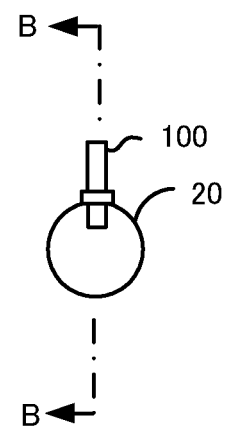

[Fig. 3]
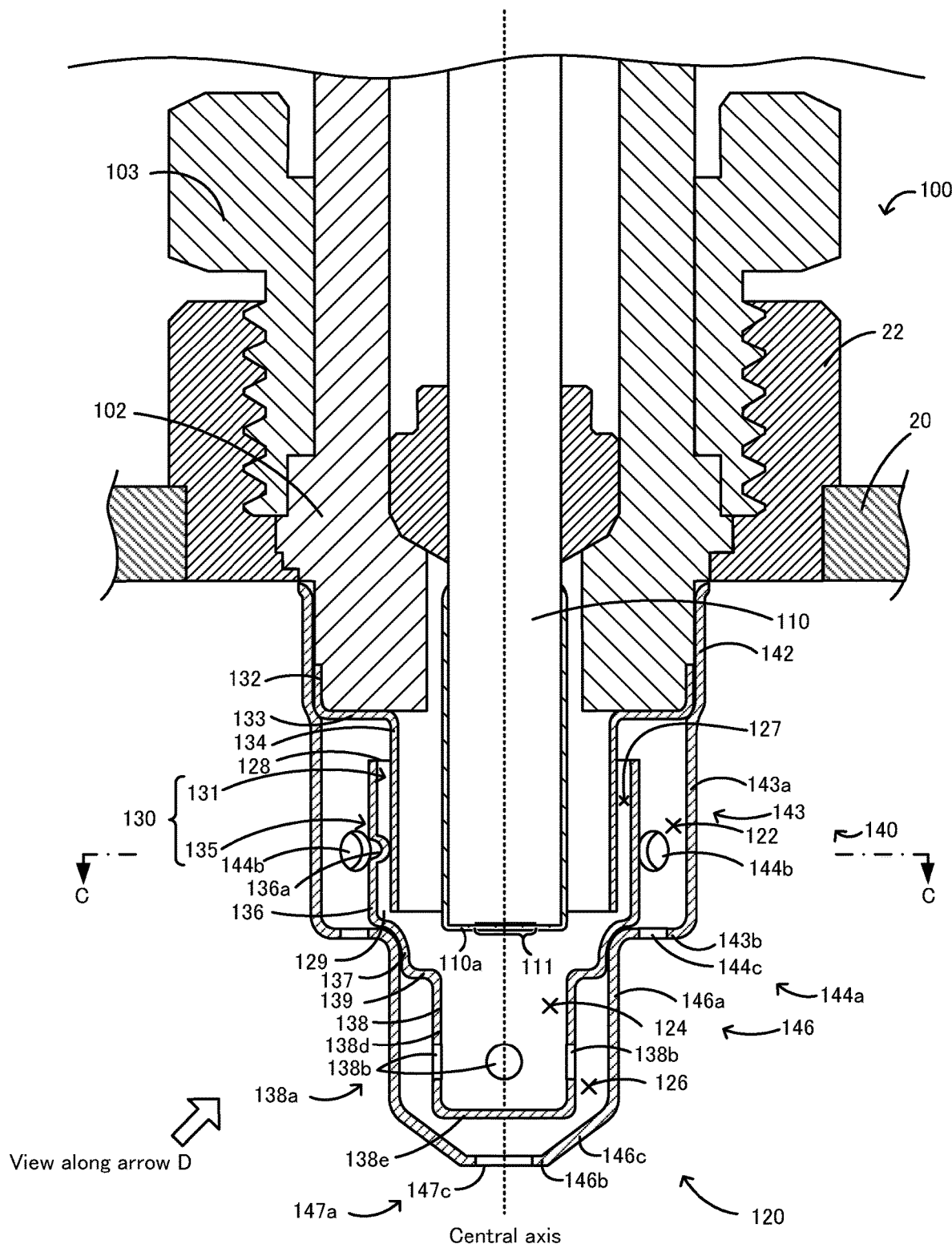

【Fig. 4】
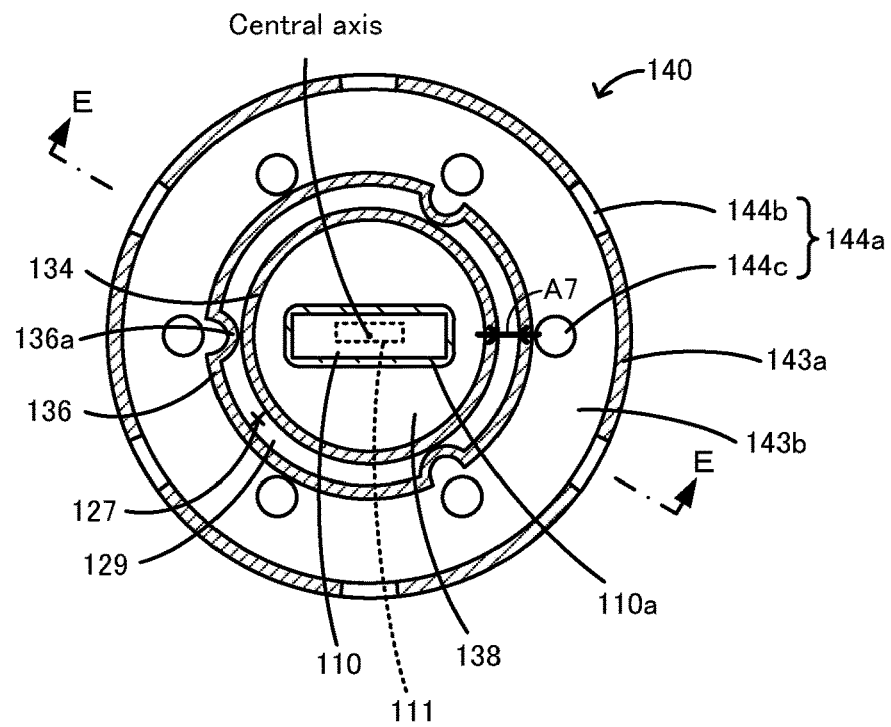
【Fig. 5】
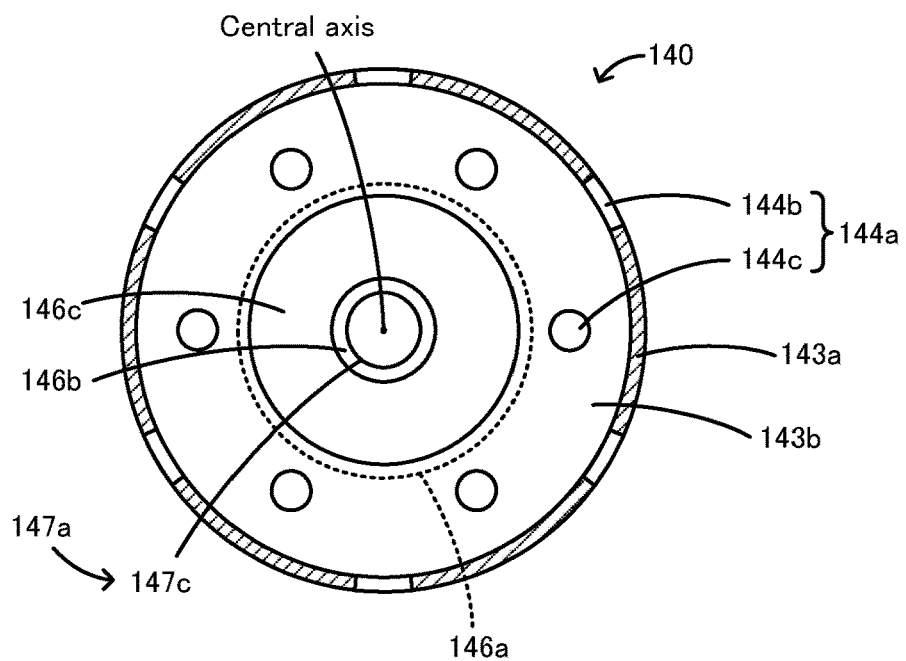

[Fig. 6]
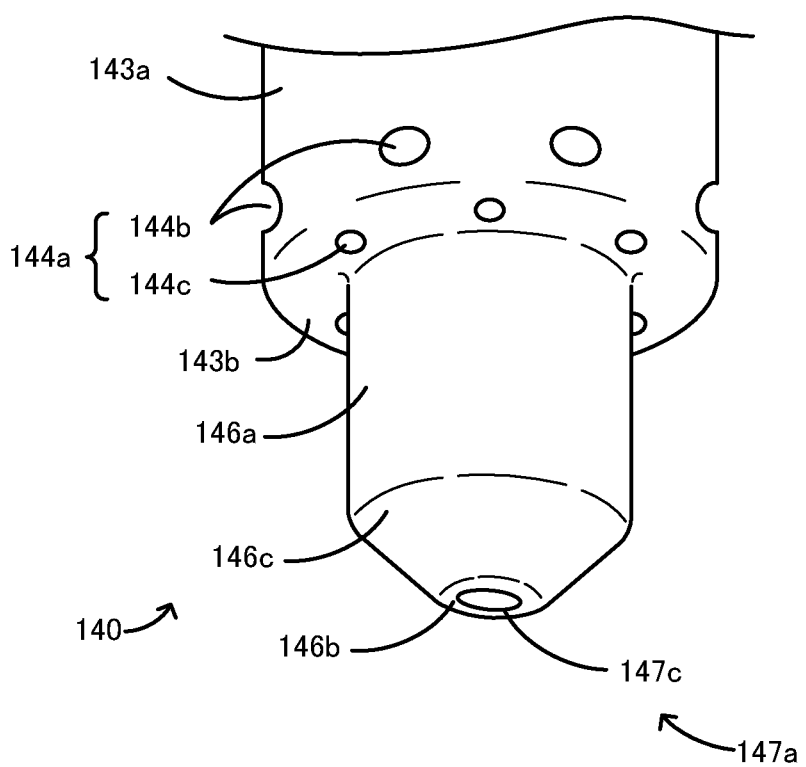

[Fig. 7]
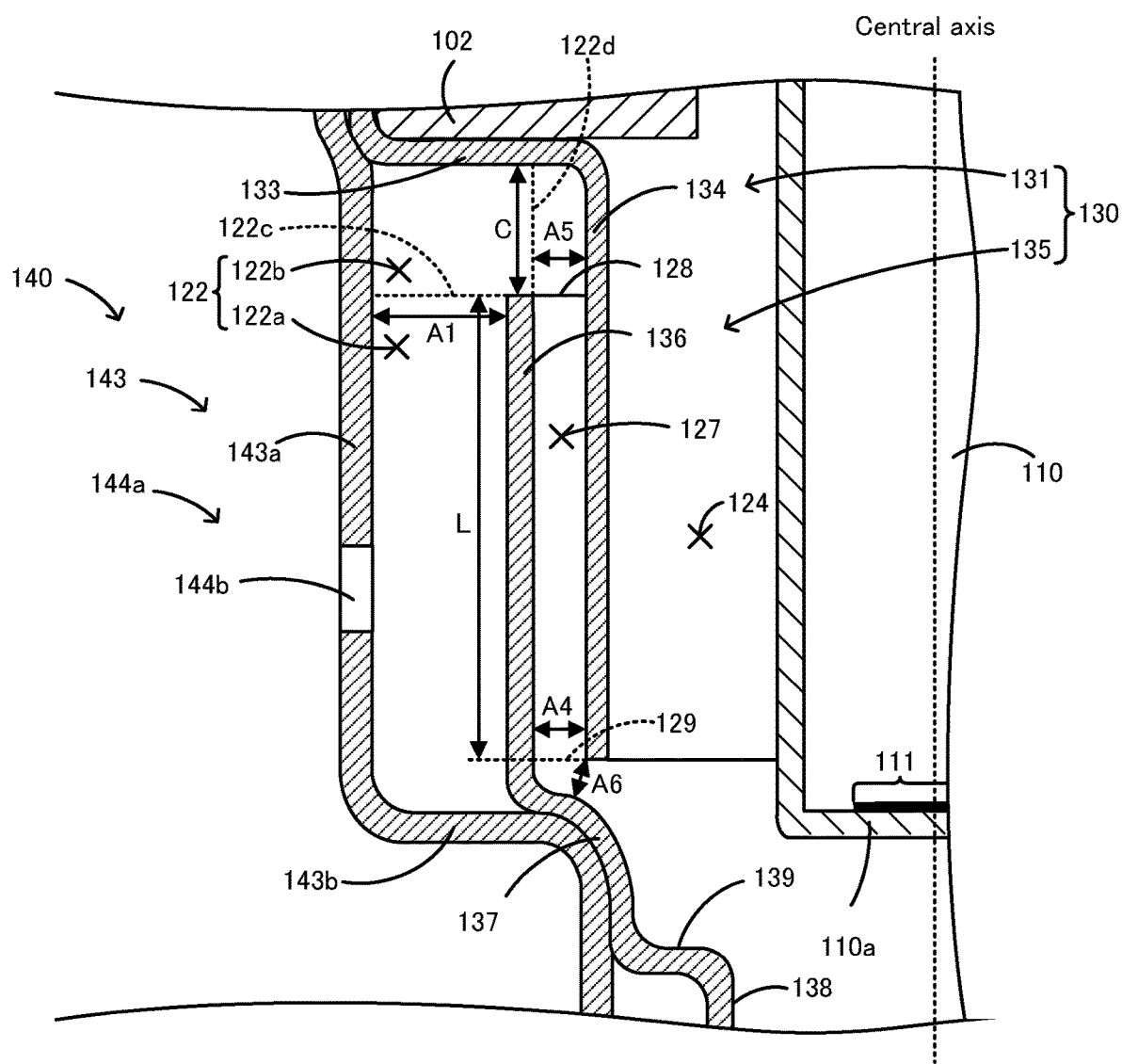

[Fig. 8]
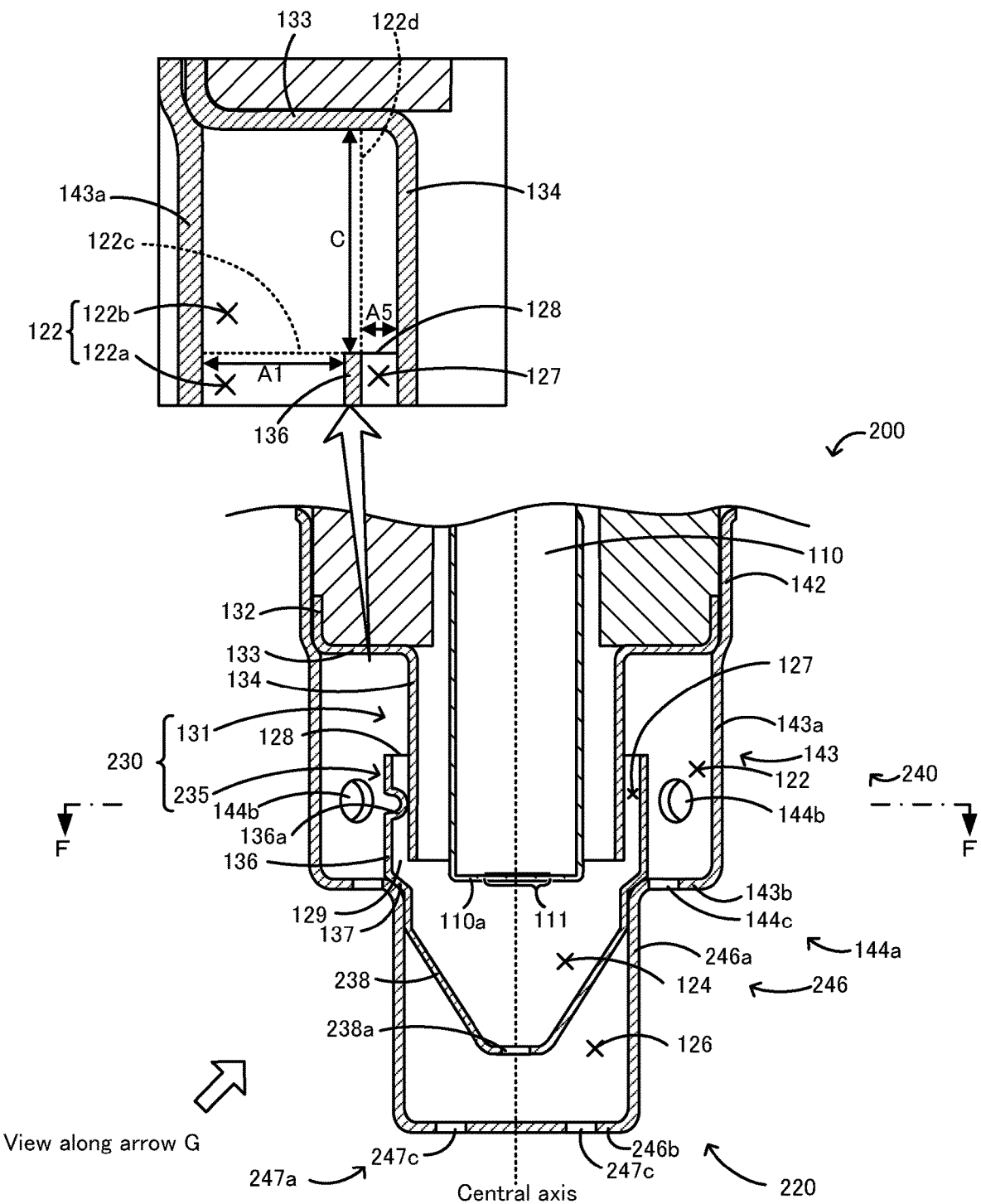

[Fig. 9]
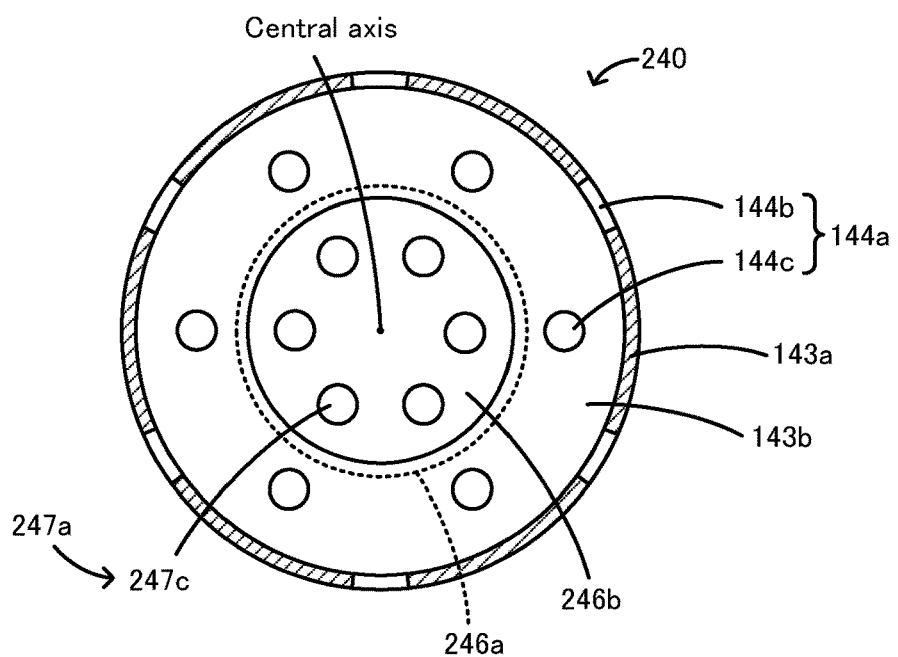
[Fig. 10]
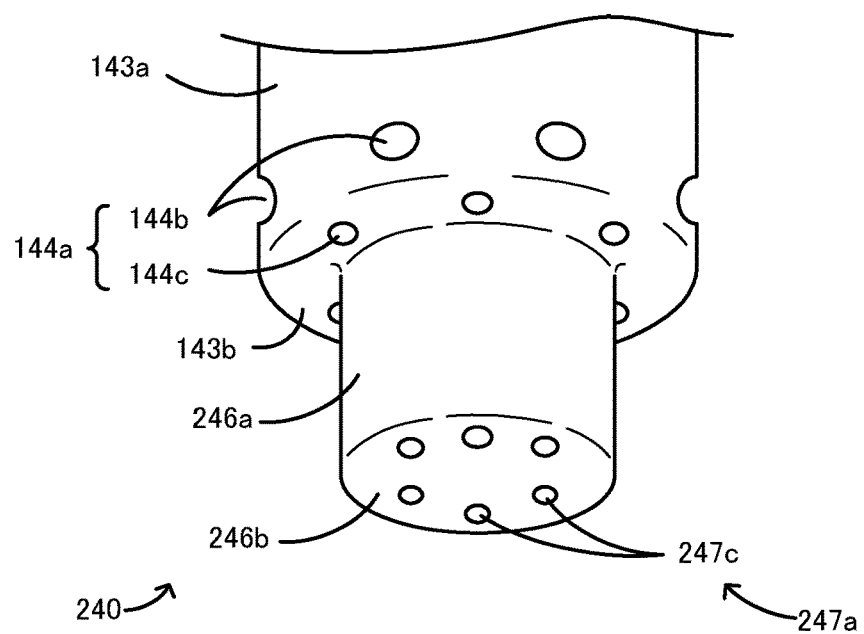

[Fig. 11]
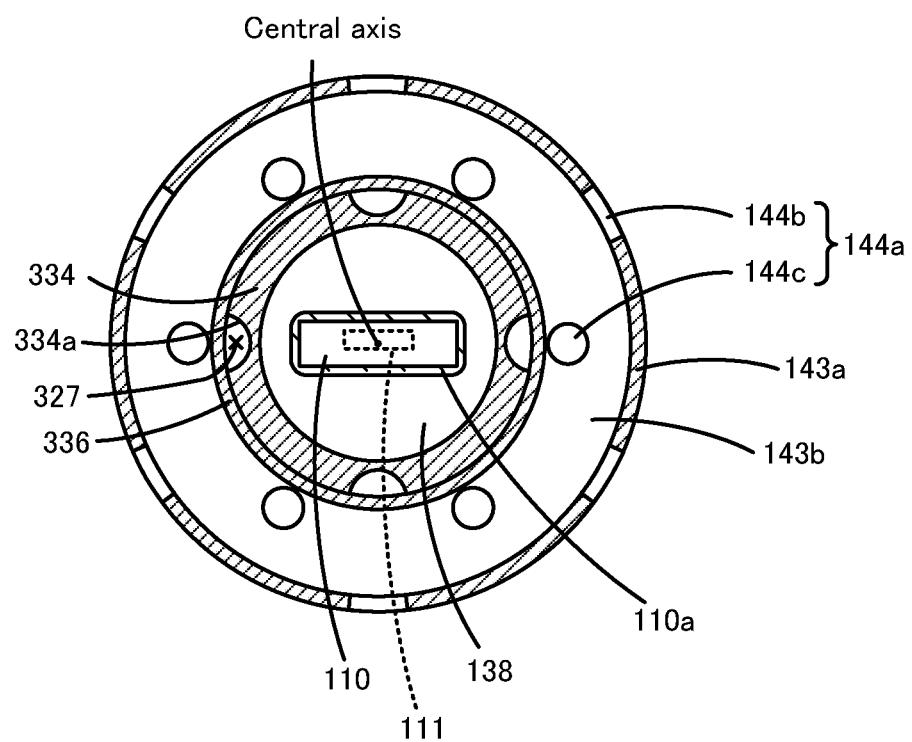

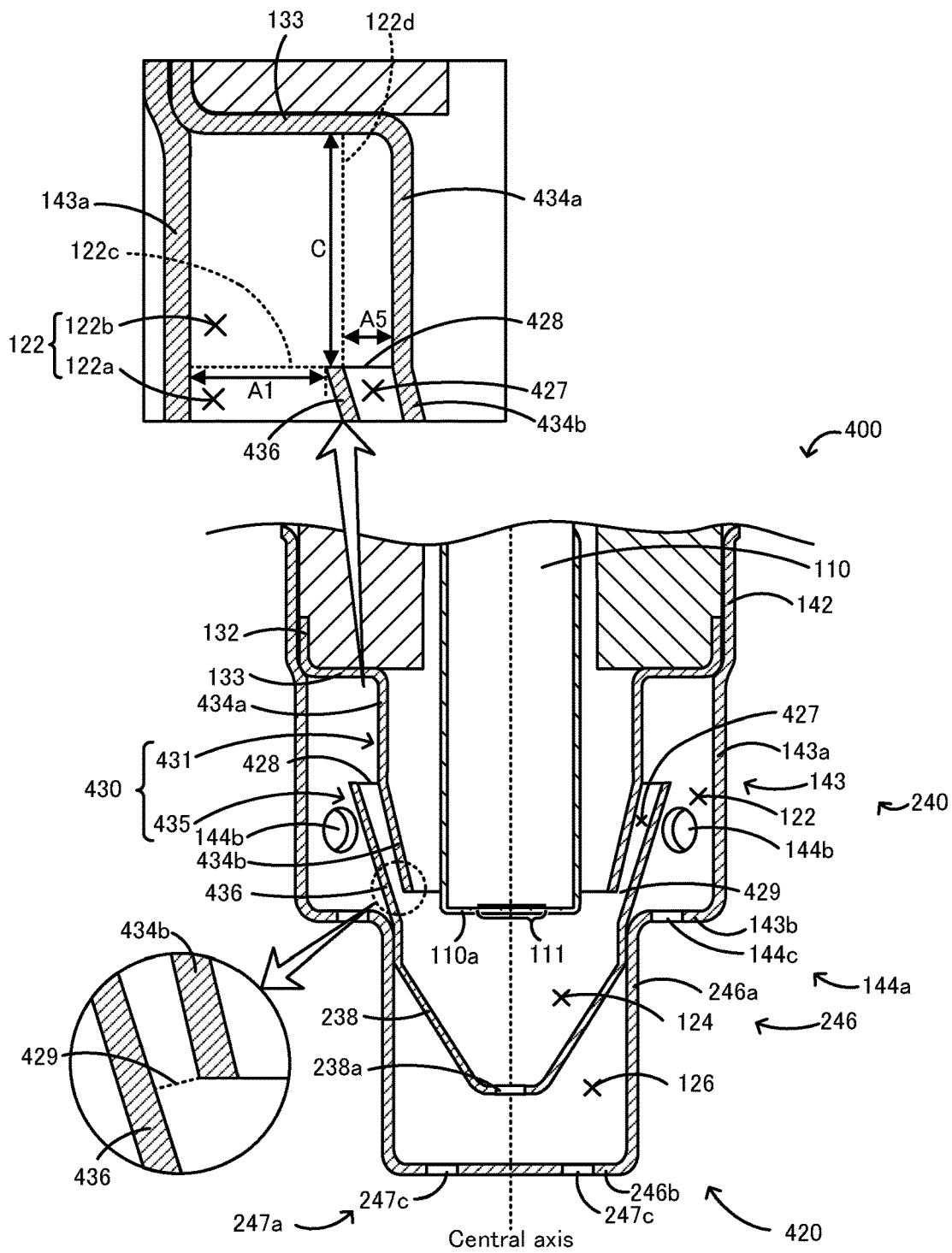
[Fig. 12]

【Fig. 13】
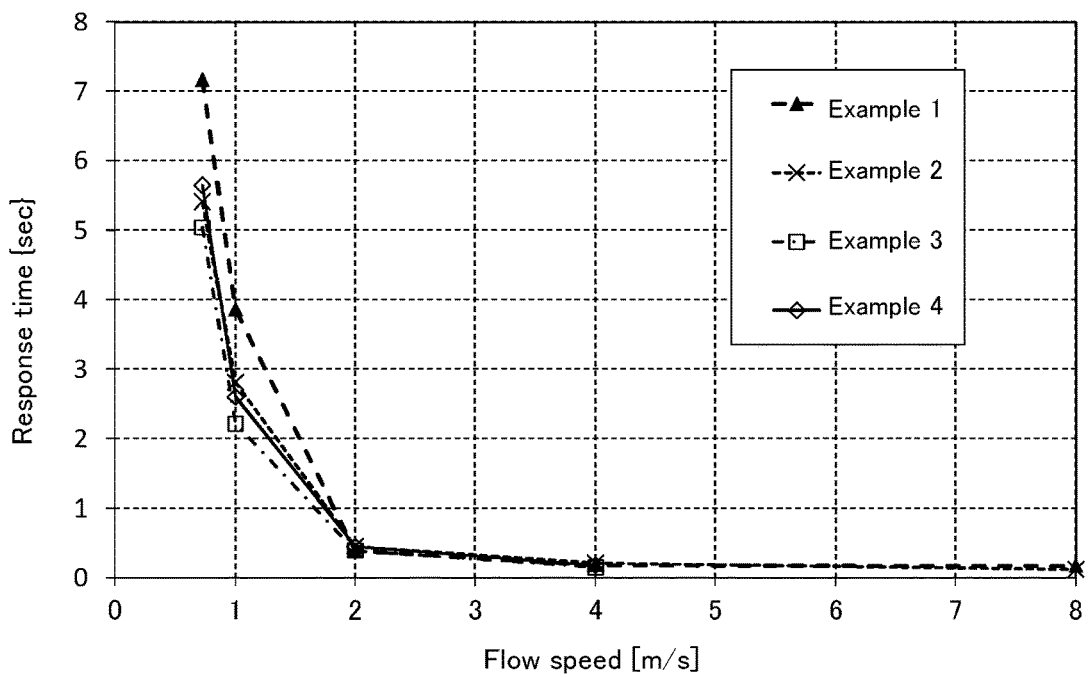
【Fig. 14】
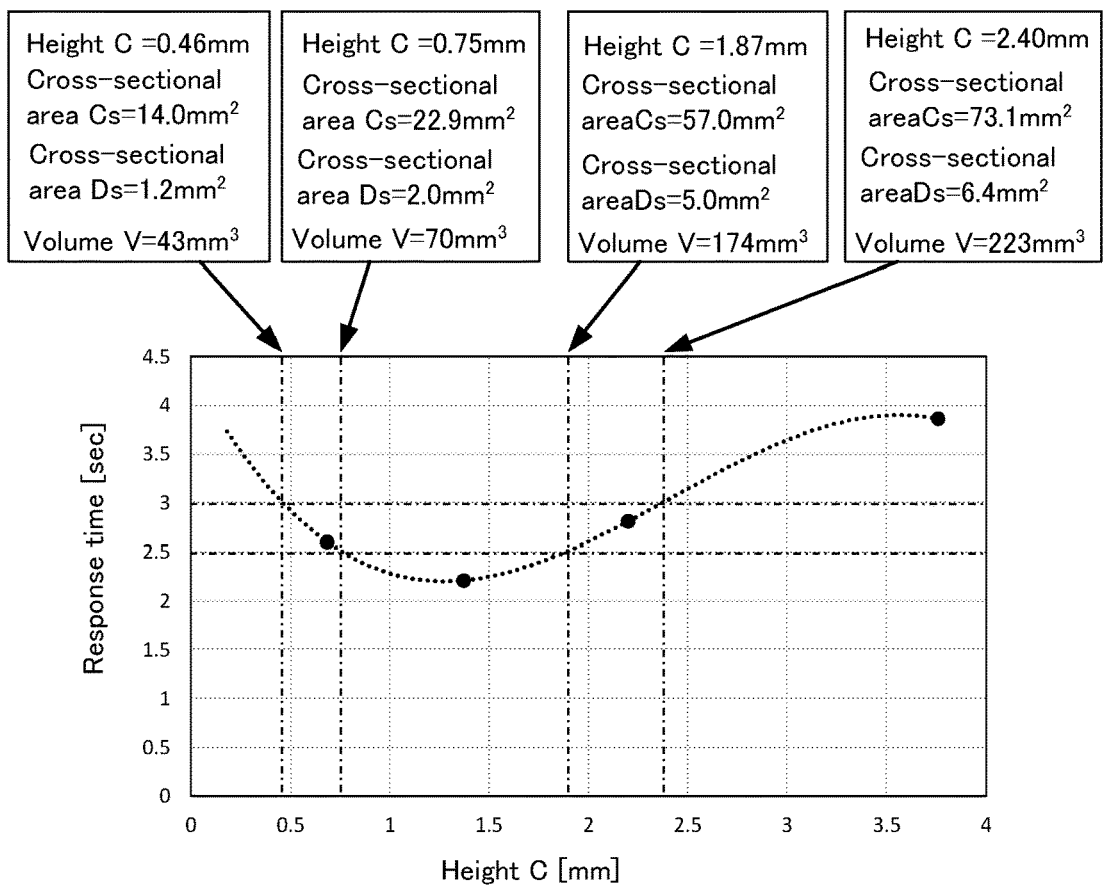

GAS SENSOR AND PROTECTIVE COVER

CROSS-REFERENCE TO RELATED APPLICATION

The present application claims priority to Japanese Patent Application No. 2019-183072, filed on Oct. 3, 2019 and Japanese Patent Application No. 2020-127253, filed on Jul. 28, 2020 the entire contents of which are incorporated herein by reference.

BACKGROUND OF THE INVENTION

1. Field of the Invention

The present invention relates to a gas sensor and a protective cover.

2. Description of the Related Art

Hitherto, a gas sensor that detects the concentration of predetermined gas, such as NOx and oxygen, in measurement-object gas, such as exhaust gas of an automobile, is known. For example, Patent Literature 1 describes a gas sensor including a sensor element, an inner protective cover in which a tip end of the sensor element is disposed, and an outer protective cover disposed outside the inner protective cover. Patent Literature 1 also describes that the response of gas concentration detection is further enhanced by setting a cross-sectional area ratio S1/S2, which is the ratio between a total cross-sectional area S1 of one or more outer inlets that are disposed in the outer protective cover and that are inlets for measurement-object gas from an outside and a total cross-sectional area S2 of one or more outer outlets that are disposed in the outer protective cover and that are outlets for measurement-object gas to the outside, to a value greater than 2.0 and less than or equal to 5.0.

CITATION LIST

Patent Literature

PTL 1: JP 2017-223620 A

SUMMARY OF THE INVENTION

Incidentally, the response of gas concentration detection also varies depending on the flow speed of measurement-object gas that flows around a gas sensor, and it has been inconvenient that the response tends to decrease when the flow speed is low (for example, lower than 2 m/s).

The present invention is made to solve such inconvenience, and it is a main object to reduce a decrease in response at a low flow speed of measurement-object gas.

To achieve the main object described above, the present invention is configured as follows.

A gas sensor according to the present invention includes: a sensor element having a gas inlet port that introduces measurement-object gas and capable of detecting a specific gas concentration of the measurement-object gas having flowed in from the gas inlet port;

a cylindrical inner protective cover having inside a sensor element chamber in which a tip end of the sensor element and the gas inlet port are disposed, and having one or more element chamber inlets that are inlets to the sensor element chamber and one or more element chamber outlets that are outlets from the sensor element chamber; and a cylindrical outer protective cover disposed outside the inner protective cover and having one or more outer inlets that are inlets for the measurement-object gas from an outside and one or more outer outlets that are outlets for the measurement-object gas to the outside, wherein the outer protective cover and the inner protective cover form, as spaces between the outer protective cover and the inner protective cover, a first gas chamber that functions as a flow channel for the measurement-object gas between the one or more outer inlets and the one or more element chamber inlets and a second gas chamber that functions as a flow channel for the measurement-object gas between the one or more outer outlets and the one or more element chamber outlets and that does not directly communicate with the first gas chamber, the inner protective cover has a cylindrical first member surrounding the sensor element, and a cylindrical second member surrounding the first member, the first member and the second member form the one or more element chamber inlets as a gap between the first member and the second member, where a direction parallel to an axial direction of the inner protective cover from the tip end of the sensor element toward a rear end of the sensor element is an upward direction and a direction from the rear end of the sensor element toward the tip end of the sensor element is a downward direction, the first gas chamber has a first space that is a space between the outer protective cover and the second member and that functions as a flow channel for the measurement-object gas from the one or more outer inlets in the upward direction and a second space that is a space above an upper end of the second member and between the outer protective cover and the first member and that functions as a flow channel for the measurement-object gas from the first space to the one or more element chamber inlets, a cross-sectional area Cs that is a flow channel cross-sectional area in the second space when the measurement-object gas passes from an outside of the second member toward an inside of the second member just above the second member is greater than or equal to 14.0 mm$^2$, and a cross-sectional area Ds that is a cross-sectional area perpendicular to a circumferential direction of the inner protective cover in the second space is greater than or equal to 0.5 mm$^2$ and less than or equal to 6.4 mm$^2$.

In this gas sensor, measurement-object gas flowing around the gas sensor flows into the first space in the first gas chamber from the one or more outer inlets of the outer protective cover, flows in the first space in the upward direction to reach the second space, flows in the second space from the outside of the second member toward the inside of the second member to reach the one or more element chamber inlets, and reaches the gas inlet port in the sensor element chamber through the one or more element chamber inlets. When the flow speed of measurement-object gas is low, the flow rate of measurement-object gas flowing in from the one or more outer inlets is low, so the flow rate of measurement-object gas that flows into the element chamber through the one or more element chamber inlets also reduces and, as a result, the response of specific gas concentration detection tends to decrease. In contrast, with the gas sensor of the present invention, the cross-sectional area Cs is greater than or equal to 14.0 mm$^2$, so measurement-object gas tends to move in the second space from the outside of the second member toward the inside of the second member. In other words, measurement-object gas in the first space becomes easy to pass through the second space toward the one or more element chamber inlets. Thus, it is possible to increase the flow rate of measurement-object gas that reaches the one or more element chamber inlets, so it is possible to suppress a decrease in the response of specific gas concentration detection at a low flow speed of measurement-object gas. When the cross-sectional area Ds is less than or equal to 6.4 mm², it is possible to suppress a decrease in response due to flow of measurement-object gas in the second space along the circumferential direction of the inner protective cover. When measurement-object gas flows in the second space along the circumferential direction of the inner protective cover, a time that is taken by measurement-object gas to pass through the second space and reach the one or more element chamber inlets extends and, as a result, the response may decrease. In contrast, when the cross-sectional area Ds is less than or equal to 6.4 mm², measurement-object gas is less likely to flow in the second space along the circumferential direction of the inner protective cover. Therefore, it is possible to suppress a decrease in response due to flow of measurement-object gas in the second space along the circumferential direction of the inner protective cover as described above. Thus, the gas sensor of the present invention is capable of reducing a decrease in response at a low flow speed of measurement-object gas. The cross-sectional area Ds is desirably smaller as described above, and the cross-sectional area Ds may be greater than or equal to 0.5 mm².

In the gas sensor of the present invention, the cross-sectional area Cs may be greater than or equal to 22.9 mm². With this configuration, measurement-object gas becomes further easy to move from the outside of the second member toward the inside of the second member in the second space, so it is possible to further suppress a decrease in response at a low flow speed of measurement-object gas.

In the gas sensor of the present invention, the cross-sectional area Ds may be less than or equal to 5.0 mm². With this configuration, it is possible to further suppress flow of measurement-object gas in the second space along the circumferential direction of the inner protective cover, so it is possible to further suppress a decrease in response at a low flow speed of measurement-object gas.

In the gas sensor of the present invention, a cross-sectional area ratio As/Bs between a cross-sectional area As of a second space inlet that is an inflow port for the measurement-object gas from the first space to the second space and a cross-sectional area Bs that is a total cross-sectional area of the one or more element chamber inlets may be greater than or equal to 1.41 and less than or equal to 4.70. When the cross-sectional area As is too small, measurement-object gas in the first space is less likely to flow into the second space and, as a result, measurement-object gas is less likely to flow into the one or more element chamber inlets. When the cross-sectional area Bs is too small, measurement-object gas in the second space is less likely to flow into the one or more element chamber inlets. In contrast, when the cross-sectional area ratio As/Bs is greater than or equal to 1.41 and less than or equal to 4.70, the balance in size between the cross-sectional areas As, Bs is good, and measurement-object gas in the first space becomes easier to pass through the second space and flows into the one or more element chamber inlets, so it is possible to further suppress a decrease in response at a low flow speed of measurement-object gas.

In the gas sensor of the present invention, a cross-sectional area As of a second space inlet that is an inflow port for the measurement-object gas from the first space to the second space may be greater than or equal to 47.3 mm² and less than or equal to 68.1 mm². In addition, a cross-sectional area Bs that is a total cross-sectional area of the one or more element chamber inlets may be greater than or equal to 14.5 mm² and less than or equal to 33.4 mm².

In the gas sensor of the present invention, the first member and the second member may form the one or more element chamber inlets such that an element-side opening that is an opening adjacent to the sensor element chamber of each of the one or more element chamber inlets is open in the downward direction. With this configuration, it is possible to reduce a situation in which measurement-object gas, flowing out from the element-side opening, perpendicularly strikes the surface (surface other than the gas inlet port) of the sensor element and to reduce a situation in which measurement-object gas passes along the surface of the sensor element over a long distance and then reaches the gas inlet port. Thus, it is possible to suppress cooling of the sensor element. In addition, cooling of the sensor element is suppressed by adjusting the orientation of the opening of the element-side opening, and the flow rate or flow speed of measurement-object gas inside the inner protective cover is not reduced, so a decrease in the response of specific gas concentration detection is also reduced. With these configurations, it is possible to suppress a decrease in the heat retaining property of the sensor element while suppressing a decrease in the response of the sensor element. Here, the phrase "the element-side opening is open in the downward direction" includes a case where each element chamber inlet is open parallel to the downward direction and a case where each element chamber inlet is open at an angle from the downward direction so as to approach the sensor element toward a lower side.

In the gas sensor of the present invention, the first member may have a first cylinder portion surrounding the sensor element, the second member may have a second cylinder portion larger in diameter than the first cylinder portion, and the one or more element chamber inlets may be a cylindrical gap between an outer peripheral surface of the first cylinder portion and an inner peripheral surface of the second cylinder portion.

A protective cover according to the present invention includes:

a gas inlet port that introduces measurement-object gas and capable of detecting a specific gas concentration of the measurement-object gas that has flowed in from the gas inlet port, the protective cover comprising:

a cylindrical inner protective cover having inside a sensor element chamber for disposing a tip end of the sensor element and the gas inlet port inside, and having one or more element chamber inlets that are inlets to the sensor element chamber and one or more element chamber outlets that are outlets from the sensor element chamber; and a cylindrical outer protective cover disposed outside the inner protective cover and having one or more outer inlets that are inlets for the measurement-object gas from an outside and one or more outer outlets that are outlets for the measurement-object gas to the outside, wherein the outer protective cover and the inner protective cover form, as spaces between the outer protective cover and the inner protective cover, a first gas chamber that functions as a flow channel for the measurement-object gas between the one or more outer inlets and the one or more element chamber inlets and a second gas chamber that functions as a flow channel for the measurement-object gas between the one or more outer outlets and the one or more element chamber outlets and that does not directly communicate with the first gas chamber, the inner protective cover includes a cylindrical first member and a cylindrical second member surrounding the first member, the first member and the second member form the one or more element chamber inlets as a gap between the first member and the second member, where a direction parallel to an axial direction of the inner protective cover from a bottom portion of the outer protective cover toward a side opposite from the bottom portion is an upward direction and a direction from the side opposite from the bottom portion of the outer protective cover toward the bottom portion is a downward direction, the first gas chamber has a first space that is a space between the outer protective cover and the second member and that functions as a flow channel for the measurement-object gas from the one or more outer inlets in the upward direction and a second space that is a space above an upper end of the second member and between the outer protective cover and the first member and that functions as a flow channel for the measurement-object gas from the first space to the one or more element chamber inlets, a cross-sectional area Cs that is a flow channel cross-sectional area in the second space when the measurement-object gas passes from an outside of the second member toward an inside of the second member just above the second member is greater than or equal to 14.0 mm$^2$, and a cross-sectional area Ds that is a cross-sectional area perpendicular to a circumferential direction of the inner protective cover in the second space is greater than or equal to 0.5 mm$^2$ and less than or equal to 6.4 mm$^2$.

By disposing the tip end of the sensor element and the gas inlet port in the sensor element chamber of the protective cover, an advantageous effect of reducing a decrease in response at a low flow speed of measurement-object gas is obtained as in the case of the above-described gas sensor of the present invention. In the protective cover of the present invention, various modes of the above-described gas sensor may be employed.

BRIEF DESCRIPTION OF THE DRAWINGS

FIG. 1 is a schematic diagram of a state where a gas sensor 100 is attached to a pipe 20.

FIG. 2 is a cross-sectional view taken along the line A-A in FIG. 1.

FIG. 3 is a cross-sectional view taken along the line B-B in FIG. 2.

FIG. 4 is a cross-sectional view taken along the line C-C in FIG. 3.

FIG. 5 is a cross-sectional view of an outer protective cover 140, taken along the line C-C in FIG. 3.

FIG. 6 is a view along the arrow D in FIG. 3.

FIG. 7 is a partially enlarged cross-sectional view taken along the line E-E in FIG. 4.

FIG. 8 is a longitudinal sectional view of a gas sensor 200 of a modification.

FIG. 9 is a cross-sectional view of an outer protective cover 240, taken along the line F-F in FIG. 8.

FIG. 10 is a view along the arrow G in FIG. 8.

FIG. 11 is a cross-sectional view showing element chamber inlets 327 of a modification.

FIG. 12 is a longitudinal sectional view of a gas sensor 400 of a modification.

FIG. 13 is a graph showing the relationship between a flow speed and a response time in each of Test Examples 1 to 4.

FIG. 14 is a graph showing the relationship between a height C, cross-sectional areas Cs, Ds, and a volume V and a response time at a flow speed of 1 m/s in each of Test Examples 1 to 4.

DETAILED DESCRIPTION OF THE INVENTION

Next, an embodiment of the present invention will be described with reference to the drawings. FIG. 1 is a schematic diagram of a state where a gas sensor 100 is attached to a pipe 20. FIG. 2 is a cross-sectional view taken along the line A-A in FIG. 1. FIG. 3 is a cross-sectional view taken along the line B-B in FIG. 2. FIG. 4 is a cross-sectional view taken along the line C-C in FIG. 3. FIG. 5 is a cross-sectional view of an outer protective cover 140, taken along the line C-C in FIG. 3. FIG. 5 corresponds to a diagram excluding a first cylinder portion 134, a second cylinder portion 136, a tip end portion 138, and a sensor element 110 from FIG. 4. FIG. 6 is a view along the arrow D in FIG. 3. FIG. 7 is an enlarged cross-sectional view of part of a cross section taken along the line E-E in FIG. 4. A direction parallel to an axial direction of a protective cover 120 from a tip end of the sensor element 110 toward a rear end of the sensor element 110 (upward direction in FIG. 3 and FIG. 7) is defined as upward direction, and a direction parallel to the axial direction of the protective cover 120 from the rear end of the sensor element 110 toward the tip end of the sensor element 110 (downward direction in FIG. 3 and FIG. 7) is defined as downward direction.

As shown in FIG. 1, the gas sensor 100 is attached inside the pipe 20 that is an exhaust pathway from an engine of a vehicle and is configured to detect a specific gas concentration that is the concentration of at least any one specific gas of gas components, such as NOx, ammonia, and $O_2$, contained in exhaust gas as measurement-object gas emitted from the engine. As shown in FIG. 2, the gas sensor 100 is fixed to the pipe 20 in a state where a central axis of the gas sensor 100 is perpendicular to the flow of measurement-object gas in the pipe 20. The gas sensor 100 may be fixed to the pipe 20 in a state where the central axis of the gas sensor 100 is perpendicular to the flow of measurement-object gas in the pipe 20 and inclined at a predetermined angle (for example, 45°) with respect to a vertical direction.

As shown in FIG. 3, the gas sensor 100 includes the sensor element 110 having a function to detect a specific gas concentration (the concentration of NOx, ammonia, $O_2$, or the like) in measurement-object gas, and the protective cover 120 that protects the sensor element 110. The gas sensor 100 includes a metal housing 102 and a metal bolt 103 provided with external thread on its outer peripheral surface. The housing 102 is inserted in a fixing member 22 welded to the pipe 20 and provided with internal thread on its inner peripheral surface, and the housing 102 is fixed in the fixing member 22 by further inserting the bolt 103 into the fixing member 22. Thus, the gas sensor 100 is fixed to the pipe 20. A direction in which measurement-object gas flows inside the pipe 20 is a direction from the left toward the right in FIG. 3.

The sensor element 110 is an element having a narrow long planar shape and has such a structure that a plurality of oxygen-ion-conductive solid electrolyte layers made of zirconia ($ZrO_2$) or the like is laminated. The sensor element 110 has a gas inlet port 111 that introduces therein measurement-object gas and is configured to be capable of detecting a specific gas concentration of measurement-object gas having flowed in from the gas inlet port 111. In the present embodiment, the gas inlet port 111 is open at the tip end surface of the sensor element 110 (the lower surface of the sensor element 110 in FIG. 3). The sensor element 110 includes inside a heater that plays a role in temperature adjustment to retain temperature by heating the sensor element 110. The structure of the sensor element 110 and the principle of detecting a specific gas concentration are known and are described in, for example, Japanese Unexamined Patent Application Publication No. 2008-164411. The tip end (the lower end in FIG. 3) and gas inlet port 111 of the sensor element 110 are disposed inside the sensor element chamber 124. A direction from the rear end of the sensor element 110 toward the tip end of the sensor element 110 (downward direction) is also referred to as tip end direction.

The sensor element 110 includes a porous protective layer 110a that covers at least part of the surface. In the present embodiment, the porous protective layer 110a is formed on five surfaces out of six surfaces of the sensor element 110 and covers almost all the surface exposed to the inside of the sensor element chamber 124. Specifically, the porous protective layer 110a covers the entire tip end surface (lower surface) at which the gas inlet port 111 is formed in the sensor element 110. The porous protective layer 110a covers a side closer to the tip end surface of the sensor element 110 on the four surfaces (the upper, lower, right, and left surfaces of the sensor element 110 in FIG. 4) connected to the tip end surface of the sensor element 110. The porous protective layer 110a plays a role in, for example, suppressing occurrence of crack in the sensor element 110 as a result of adhesion of moisture or the like in measurement-object gas. The porous protective layer 110a also plays a role in suppressing adhesion of an oil component and the like contained in measurement-object gas to an electrode (not shown) or the like of the surface of the sensor element 110. The porous protective layer 110a is made of, for example, a porous material, such as alumina porous material, zirconia porous material, spinel porous material, cordierite porous material, titania porous material, and magnesia porous material. The porous protective layer 110a may be formed by, for example, plasma spraying, screen printing, dipping, or the like. The porous protective layer 110a also covers the gas inlet port 111; however, since the porous protective layer 110a is a porous material, measurement-object gas is able to flow through the inside of the porous protective layer 110a and reach the gas inlet port 111. The thickness of the porous protective layer 110a is, for example, 100 μm to 700 μm.

The protective cover 120 is disposed so as to surround the sensor element 110. The protective cover 120 has a closed-end cylindrical inner protective cover 130 that covers the tip end of the sensor element 110 and a closed-end cylindrical outer protective cover 140 that covers the inner protective cover 130. A first gas chamber 122 and a second gas chamber 126 are formed as spaces surrounded by the inner protective cover 130 and the outer protective cover 140, and a sensor element chamber 124 is formed as a space surrounded by the inner protective cover 130. The central axes of the gas sensor 100, the sensor element 110, the inner protective cover 130, and the outer protective cover 140 are coaxial with one another. The protective cover 120 is made of metal (for example, stainless steel, such as SUS310S).

The inner protective cover 130 includes a first member 131 and a second member 135. The first member 131 has a cylindrical large-diameter portion 132, a cylindrical first cylinder portion 134 smaller in diameter than the large-diameter portion 132, and a stepped portion 133 that connects the large-diameter portion 132 and the first cylinder portion 134. The first cylinder portion 134 surrounds the sensor element 110. The second member 135 has a second cylinder portion 136 larger in diameter than the first cylinder portion 134, a tip end portion 138 located on a side in the tip end direction (downward direction) of the sensor element 110 with respect to the second cylinder portion 136, a stepped portion 139 disposed so as to be connected to the upper end of the tip end portion 138 and protruding outward from the outer peripheral surface of the tip end portion 138, and a connection portion 137 connecting the lower end of the second cylinder portion 136 and the stepped portion 139. The tip end portion 138 has a side portion 138d and a bottom portion 138e. The tip end portion 138 has one or more element chamber outlets 138a that communicate with the sensor element chamber 124 and the second gas chamber 126 and that are outlets for measurement-object gas from the sensor element chamber 124. The element chamber outlets 138a include a plurality of (four in the present embodiment) horizontal holes 138b formed at equal intervals at the side portion 138d. The element chamber outlets 138a are not disposed at the bottom portion 138e of the tip end portion 138. The diameter of each element chamber outlet 138a is, for example, 0.5 mm to 2.6 mm. In the present embodiment, the diameter of each of the plurality of horizontal holes 138b is set to the same value. The element chamber outlets 138a are formed on a side in the tip end direction (downward direction) of the sensor element 110 with respect to the gas inlet port 111. In other words, the element chamber outlets 138a are located away (in the downward direction) from the gas inlet port 111 when viewed from the rear end of the sensor element 110 (the upper end (not shown) of the sensor element 110 in FIG. 3).

The large-diameter portion 132, the first cylinder portion 134, the second cylinder portion 136, and the tip end portion 138 have the same central axis. The inner peripheral surface of the large-diameter portion 132 is in contact with the housing 102. Thus, the first member 131 is fixed to the housing 102. In the second member 135, the outer peripheral surface of the connection portion 137 is in contact with the inner peripheral surface of the outer protective cover 140 and is fixed to the inner peripheral surface of the outer protective cover 140 by welding or the like. The second member 135 may be fixed by forming the outside diameter of the tip end side (lower end side) of the connection portion 137 so as to be slightly larger than the inside diameter of the tip end portion 146 of the outer protective cover 140 and press-fitting the tip end portion of the connection portion 137 into the tip end portion 146.

A plurality of protruding portions 136a that protrude toward the outer peripheral surface of the first cylinder portion 134 and that are in contact with the outer peripheral surface are formed on the inner peripheral surface of the second cylinder portion 136. As shown in FIG. 4, three protruding portions 136a are provided and are disposed equally on the inner peripheral surface of the second cylinder portion 136 along the circumferential direction. Each protruding portion 136a is formed in a substantially semi-spherical shape. With the thus configured protruding portions 136a, the positional relation between the first cylinder portion 134 and the second cylinder portion 136 is easily fixed by the protruding portions 136a. It is desirable that the protruding portions 136a press the outer peripheral surface of the first cylinder portion 134 radially inward. With this configuration, it is possible to further reliably fix the positional relation between the first cylinder portion 134 and the second cylinder portion 136 with the protruding portions 136a. The number of the protruding portions 136a is not limited to three and may be two or may be more than or equal to four. Because fixing of the first cylinder portion 134 to the second cylinder portion 136 tends to be stable, it is desirable that the number of the protruding portions 136a be more than or equal to three.

The inner protective cover 130 forms an element chamber inlet 127 (see FIG. 3, FIG. 4, and FIG. 7) that is a gap between the first member 131 and the second member 135 and that is an inlet for measurement-object gas into the sensor element chamber 124. More specifically, the element chamber inlet 127 is formed as a cylindrical gap (gas flow channel) between the outer peripheral surface of the first cylinder portion 134 and the inner peripheral surface of the second cylinder portion 136. The element chamber inlet 127 has an outer opening 128 that is an opening adjacent to the first gas chamber 122 that is a space in which the outer inlets 144a are disposed, and an element-side opening 129 that is an opening adjacent to the sensor element chamber 124 that is a space in which the gas inlet port 111 is disposed. The outer opening 128 is formed on the rear end side (upper side) of the sensor element 110 with respect to the element-side opening 129. Therefore, in the pathway of measurement-object gas from the outer inlets 144a to the gas inlet port 111, the element chamber inlet 127 is a flow channel from the rear end side (upper side) of the sensor element 110 toward the tip end side (lower side). The element chamber inlet 127 is a flow channel parallel to a rear end-tip end direction (a flow channel parallel to the up-down direction) of the sensor element 110.

The element-side opening 129 is open in a direction from the rear end of the sensor element 110 toward the tip end of the sensor element 110 (downward direction) and is open parallel to the rear end-tip end direction (up-down direction) of the sensor element 110. In other words, the element-side opening 129 is open parallel to the downward direction. Therefore, the sensor element 110 is disposed at a position other than a region that is an imaginary extension of the element chamber inlet 127 from the element-side opening 129 (a region just below the element-side opening 129 in FIG. 3 and FIG. 7). Thus, it is possible to reduce a situation in which measurement-object gas flowing out from the element-side opening 129 directly strikes the surface of the sensor element 110, so it is possible to suppress cooling of the sensor element 110.

The outer peripheral surface of the first cylinder portion 134 and the inner peripheral surface of the second cylinder portion 136 are spaced apart by a distance A4 (see FIG. 7) in the radial direction of the cylinder at the element-side opening 129 and are spaced apart by a distance A5 in the radial direction of the cylinder at the outer opening 128. The outer peripheral surface of the first cylinder portion 134 and the inner peripheral surface of the second cylinder portion 136 are spaced apart by a distance A7 in a part (the cross section shown in FIG. 4) where the protruding portions 136a and the first cylinder portion 134 contact with each other. The distance A4, the distance A5, and the distance A7 each are, for example, 0.3 mm to 2.4 mm. The distance A4, the distance A5, and the distance A7 each may be greater than or equal to 0.51 mm or may be less than or equal to 1.18 mm. By adjusting the values of the distance A4 and the distance A5, it is possible to adjust the opening area of the element-side opening 129 and the opening area of the outer opening 128. In the present embodiment, it is assumed that the distance A4, the distance A5, and the distance A7 are equal to one another and the opening area of the element-side opening 129 and the opening area of the outer opening 128 are equal to each other. In the present embodiment, the distance A4 (the distance A5, or the distance A7) is equal to a value of half of the difference between the outside diameter of the first cylinder portion 134 and the inside diameter of the second cylinder portion 136. A distance in the up-down direction between the element-side opening 129 and the outer opening 128, that is, a distance L of the element chamber inlet 127 in the up-down direction (which corresponds to the pathway length of the element chamber inlet 127) is, for example, greater than 0 mm and less than or equal to 6.6 mm. The distance L may be greater than or equal to 3 mm or may be less than or equal to 5 mm. A minimum distance between the lower end of the first cylinder portion 134 and the connection portion 137 is set to a distance A6 (see FIG. 7). The distance A6 may be a value greater than the distance A4, the distance A5, or the distance A7 or may be a value equal to the distance A4, the distance A5, or the distance A7 or may be a value less than the distance A4, the distance A5, or the distance A7.

As shown in FIG. 3, the outer protective cover 140 has a cylindrical large-diameter portion 142, a cylindrical body portion 143 connected to the large-diameter portion 142 and smaller in diameter than the large-diameter portion 142, and a closed-end cylindrical tip end portion 146 smaller in inside diameter than the body portion 143. The body portion 143 has a side portion 143a having a side surface along a central axis direction (up-down direction) of the outer protective cover 140, and a stepped portion 143b that is a bottom portion of the body portion 143 and that connects the side portion 143a and the tip end portion 146. The central axes of the large-diameter portion 142, the body portion 143, and the tip end portion 146 all are the same as the central axis of the inner protective cover 130. The large-diameter portion 142 is in contact with the housing 102 and the large-diameter portion 132 on its inner peripheral surface. Thus, the outer protective cover 140 is fixed to the housing 102. The body portion 143 is located so as to cover the outer circumference of the first cylinder portion 134 and the second cylinder portion 136. The large-diameter portion 142 and the body portion 143 may have diameters equal to each other. The tip end portion 146 is located so as to cover the tip end portion 138, and the inner peripheral surface is in contact with the outer peripheral surface of the connection portion 137. The tip end portion 146 has a side portion 146a having a side surface along the central axis direction (up-down direction) of the outer protective cover 140 and of which the outside diameter is smaller than the inside diameter of the side portion 143a, a bottom portion 146b that is the bottom portion of the outer protective cover 140, and a tapered portion 146c that connects the side portion 146a and the bottom portion 146b and that reduces in diameter from the side portion 146a toward the bottom portion 146b. The tip end portion 146 is located on the side in the tip end direction (on the lower side) with respect to the body portion 143. The outer protective cover 140 has one or more (in the present embodiment, multiple and, specifically, 12) outer inlets 144a that are formed in the body portion 143 and that are inlets for measurement-object gas from the outside, and one or more outer outlets 147a that are formed in the tip end portion 146 and that are outlets for measurement-object gas to the outside.

The outer inlets 144a are holes that communicate with the outer side (outside) of the outer protective cover 140 and the first gas chamber 122. The outer inlets 144a include a plurality of (in the present embodiment, six) horizontal holes 144b formed at equal intervals in the side portion 143a, and a plurality of (in the present embodiment, six) vertical holes 144c formed at equal intervals in the stepped portion 143b (see FIG. 3 to FIG. 6). The outer inlets 144a (horizontal holes 144b and vertical holes 144c) are holes perforated in a circular shape (perfect circle). The diameter of each of the 12 outer inlets 144a is, for example, 0.5 mm to 2 mm. The diameter of each outer inlet 144a may be less than or equal to 1.5 mm. In the present embodiment, the diameter of each of the plurality of horizontal holes 144b is the same value, and the diameter of each of the plurality of vertical holes 144c is the same value. The diameter of each horizontal hole 144b is greater than the diameter of each vertical hole 144c. As shown in FIG. 4 and FIG. 5, the outer inlets 144a are formed such that the horizontal holes 144b and the vertical holes 144c are alternately located at equal intervals along the circumferential direction of the outer protective cover 140. In other words, an angle formed between a line connecting the center of each horizontal hole 144b and the central axis of the outer protective cover 140 and a line connecting the center of the vertical hole 144c adjacent to that horizontal hole 144b and the central axis of the outer protective cover 140 in FIG. 4 and FIG. 5 is 30° (360°/12).

The outer outlet 147a is a hole that communicates with the outer side (outside) of the outer protective cover 140 and the second gas chamber 126. The outer outlet 147a includes one vertical hole 147c formed at the center of the bottom portion 146b of the tip end portion 146 (see FIG. 3, FIG. 5, and FIG. 6). Different from the outer inlets 144a, the outer outlet 147a is not disposed at the side portion of the outer protective cover 140 (here, the side portion 146a of the tip end portion 146). The outer outlet 147a (here, the vertical hole 147c) is a hole perforated in a circular shape (perfect circle). The diameter of the outer outlet 147a is, for example, 0.5 mm to 2.5 mm. The diameter of the outer outlet 147a may be less than or equal to 1.5 mm. In the present embodiment, the diameter of the vertical hole 147c is set to a value greater than the diameter of the horizontal hole 144b or the vertical hole 144c.

The outer protective cover 140 and the inner protective cover 130 form the first gas chamber 122 as a space between the body portion 143 and the inner protective cover 130. More specifically, the first gas chamber 122 is a space surrounded by the stepped portion 133, the first cylinder portion 134, the second cylinder portion 136, the side portion 143a, and the stepped portion 143b. The sensor element chamber 124 is formed as a space surrounded by the inner protective cover 130. The outer protective cover 140 and the inner protective cover 130 form the second gas chamber 126 as a space between the tip end portion 146 and the inner protective cover 130. More specifically, the second gas chamber 126 is a space surrounded by the tip end portion 138 and the tip end portion 146. Since the inner peripheral surface of the tip end portion 146 is in contact with the outer peripheral surface of the connection portion 137, the first gas chamber 122 and the second gas chamber 126 do not directly communicate with each other.

As shown in FIG. 7, the first gas chamber 122 has a first space 122a and a second space 122b. The first space 122a is a space between the outer protective cover 140 and the second member 135 of the inner protective cover 130 and functions as a flow channel for measurement-object gas that flows in the upward direction from the outer inlets 144a. The first space 122a is, more specifically, a space surrounded by the side portion 143a, the stepped portion 143b, and the second cylinder portion 136 and is a space below the upper end of the second member 135 (here, the upper end of the second cylinder portion 136). The first space 122a is a cylindrical gap between the inner peripheral surface of the outer protective cover 140 and the outer peripheral surface of the second cylinder portion 136. The second space 122b is a space above the upper end of the second member 135 (here, the upper end of the second cylinder portion 136) between the outer protective cover 140 and the first member 131 (here, the first cylinder portion 134). The second space 122b functions as a flow channel for measurement-object gas from the first space 122a to the element chamber inlet 127. The second space 122b is a cylindrical gap between the inner peripheral surface of the outer protective cover 140 and the outer peripheral surface of the first cylinder portion 134.

An inflow port for measurement-object gas from the first space 122a to the second space 122b is referred to as second space inlet 122c. The second space inlet 122c is a ring-shaped gap between the inner peripheral surface of the outer protective cover 140 and the upper end of the outer peripheral surface of the second cylinder portion 136. All the outer inlets 144a are located below the second space inlet 122c. In other words, all the outer inlets 144a are located below the upper end of the second member 135 (here, the upper end of the second cylinder portion 136). The width of the second space inlet 122c in the radial direction, that is, a difference between the radius of the inner peripheral surface of the outer protective cover 140 and the radius of the upper end of the outer peripheral surface of the second cylinder portion 136, is referred to as distance A1 (see FIG. 7). The cross-sectional area (opening area) of the second space inlet 122c is referred to as cross-sectional area As. The cross-sectional area As is the area of a plane perpendicular to the up-down direction. In the present embodiment, the cross-sectional area As=(the area of a circle having the inside diameter of the side portion 143a as a diameter)−(the area of a circle having the outside diameter of the second cylinder portion 136 as a diameter). The distance A1 may be, for example, greater than or equal to 1.18 mm or may be less than or equal to 1.85 mm. The distance A1 may be a value greater than or equal to the distance A4, the distance A5, or the distance A7. A ratio A/A4 may be greater than or equal to 1.0 and less than or equal to 3.63. A ratio A/A5 and a ratio A/A7 each may also be similarly greater than or equal to 1.0 and less than or equal to 3.63. The cross-sectional area As may be, for example, greater than or equal to 47.3 mm$^2$ or may be less than or equal to 68.1 mm$^2$.

The above-described outer opening 128 is also an outlet (second space outlet) from the second space 122b to the element chamber inlet 127. The cross-sectional area (flow channel cross-sectional area) of the element chamber inlet 127 is referred to as cross-sectional area Bs. The cross-sectional area Bs is defined as an area in a direction perpendicular to the direction of measurement-object gas (here, downward direction) that passes through the element chamber inlet 127. When the flow channel cross-sectional area for measurement-object gas in the element chamber inlet 127 is not constant, the minimum value is set for the cross-sectional area Bs. For example, in the present embodiment, since the distances A4 and A5 are equal to each other, the outer opening 128 and the element-side opening 129 have an equal opening area (=flow channel cross-sectional area); however, the flow channel cross-sectional area in a part where the protruding portions 136a are present in the element chamber inlet 127 is less than these opening areas. For this reason, in the present embodiment, the cross-sectional area of the element chamber inlet 127 in a cross section in which the protruding portions 136a protrude the most, that is, the cross section shown in FIG. 4, in the element chamber inlet 127 is set for the cross-sectional area Bs. Therefore, in the present embodiment, the cross-sectional area Bs=(the area of a circle having the inside diameter of the second cylinder portion 136 as a diameter)−(the area of a circle having the outside diameter of the first cylinder portion 134 as a diameter)−(the absolute value of a reduction in the cross-sectional area of the element chamber inlet 127 due to the protruding portions 136a in the cross section of FIG. 4)×(the number of protruding portions 136a). The cross-sectional area Bs may be, for example, greater than or equal to 14.5 mm$^2$ or may be less than or equal to 33.4 mm$^2$.

In the second space 122b, a cross section at the time when measurement-object gas passes from the outside of the second member 135 toward the inside of the second member 135 (passes from the left to the right in FIG. 7) just above the second member 135 (here, just above the second cylinder portion 136) is referred to as flow channel cross section 122d. The length of the flow channel cross section 122d in the up-down direction is referred to as height C, and the cross-sectional area of the flow channel cross section 122d is referred to as cross-sectional area Cs. The cross-sectional area Cs is equal to the area of the outer peripheral surface of a circular cylinder having the height C with a diameter equal to the inside diameter of the second cylinder portion 136. In other words, the cross-sectional area Cs=(the inside diameter of the second cylinder portion 136)×π×(height C). The flow channel cross section 122d is a cross section perpendicular to a radial direction toward the center of the inner protective cover 130 and just above the second cylinder portion 136 in the second space 122b and is determined as a cross section at a position where the cross-sectional area is minimum just above the second member 135. For example, in the present embodiment, the cross-sectional area of the second space 122b, perpendicular to the radial direction, is smaller at a position just above the inner peripheral surface of the second cylinder portion 136 than a position just above the outer peripheral surface of the second cylinder portion 136. For this reason, a cross section perpendicular to the radial direction of the inner protective cover 130 and just above the inner peripheral surface of the second cylinder portion 136 in the second space 122b is determined as the flow channel cross section 122d. The height C may be, for example, greater than or equal to 0.47 mm or may be greater than or equal to 0.75 mm. The height C may be less than or equal to 2.35 mm or may be less than or equal to 1.87 mm.

In the second space 122b, a cross-sectional area perpendicular to the circumferential direction of the inner protective cover 130 is referred to as cross-sectional area Ds. The cross-sectional area Ds is the area of the second space 122b illustrated in the cross section of FIG. 7 (substantially a rectangular area). In the present embodiment, the cross-sectional area Ds={(the inside diameter of the side portion 143a)−(the outside diameter of the first cylinder portion 134)}+2×(height C). In other words, the cross-sectional area Ds={A1+A5+(the thickness of the second cylinder portion 136)}×(height C).

The volume V of the second space 122b may be, for example, greater than or equal to 43 mm$^3$ or may be greater than or equal to 70 mm$^3$. The volume V of the second space 122b may be, for example, less than or equal to 223 mm$^3$ or may be less than or equal to 174 mm$^3$. In the present embodiment, volume V={(the area of a circle having the inside diameter of the side portion 143a as a diameter)−(the area of a circle having the outside diameter of the first cylinder portion 134 as a diameter)}×(height C).

Here, the flow of measurement-object gas inside the protective cover 120 at the time when the gas sensor 100 detects a specific gas concentration will be described. Measurement-object gas that flows in the pipe 20 initially passes through at least any one of the plurality of outer inlets 144a (the horizontal holes 144b and the vertical holes 144c) and flows into the first gas chamber 122. Subsequently, measurement-object gas flows from the first gas chamber 122 into the element chamber inlet 127 via the outer opening 128, passes through the element chamber inlet 127, flows out from the element-side opening 129, and flows into the sensor element chamber 124. Measurement-object gas having flowed from the element-side opening 129 into the sensor element chamber 124 at least partially reaches the gas inlet port 111 of the sensor element 110. When measurement-object gas reaches the gas inlet port 111 and flows into the inside of the sensor element 110, the sensor element 110 generates an electrical signal (voltage or current) according to a specific gas concentration in the measurement-object gas, and the specific gas concentration is detected based on the electrical signal. Measurement-object gas in the sensor element chamber 124 flows into the second gas chamber 126 through at least any one of the element chamber outlets 138a (the horizontal holes 138b) and flows out from there to the outside through the outer outlet 147a. The output of a heater inside the sensor element 110 is controlled by a controller (not shown) such that the sensor element 110 is maintained at a predetermined temperature.

Of the above-described flow of measurement-object gas, flow in the first gas chamber 122 and in the element chamber inlet 127 will be described in detail. Measurement-object gas having flowed into the outer protective cover 140 from the outer inlets 144a initially flows into the first space 122a in the first gas chamber 122 and flows in the upward direction in the first space 122a. Subsequently, measurement-object gas reaches the inside of the second space 122b from the second space inlet 122c, flows in the second space 122b from the outside of the second member 135 toward the inside of the second member 135, that is, flows in the second space 122b in the radial direction toward the central axis of the protective cover 120, and reaches the outer opening 128 of the element chamber inlet 127. Then, measurement-object gas flows in the downward direction from the outer opening 128 in the element chamber inlet 127 and reaches the inside of the sensor element chamber 124 from the element-side opening 129.

Generally, when the flow speed of measurement-object gas is low (for example, lower than 2 m/s), the flow rate of measurement-object gas flowing in from the outer inlets 144a is low, so the flow rate of measurement-object gas that flows into the sensor element chamber 124 through the element chamber inlet 127 also reduces and, as a result, the response of specific gas concentration detection tends to decrease. In contrast, with the gas sensor 100 of the present embodiment, the above-described cross-sectional area Cs is greater than or equal to 14.0 mm$^2$, so measurement-object gas tends to move from the outside of the second member 135 toward the inside of the second member 135 in the second space 122b. In other words, measurement-object gas in the first space 122a tends to pass through the second space 122b toward the element chamber inlet 127. Thus, it is possible to increase the flow rate of measurement-object gas that reaches the element chamber inlet 127, so it is possible to suppress a decrease in the response of specific gas concentration detection at a low flow speed of measurement-object gas.

With the gas sensor 100 of the present embodiment, when the cross-sectional area Ds is less than or equal to 6.4 mm$^2$, it is possible to suppress a decrease in response due to flow of measurement-object gas in the second space 122b along the circumferential direction of the inner protective cover 130. Generally, when measurement-object gas flows in the second space 122b along the circumferential direction of the inner protective cover 130, a time that is taken by measurement-object gas to pass through the second space 122b and reach the element chamber inlet 127 extends and, as a result, the response may decrease. Generally, when a plurality of the outer inlets 144a is present, there can be a case where measurement-object gas flows out from the outer inlet 144a located at a position near the downstream side of measurement-object gas flowing around the outer protective cover 140 among the plurality of outer inlets 144a flows out to the outside. Since, for example, in FIG. 3, measurement-object gas flows around the outer protective cover 140 from the left to the right, the horizontal hole 144b, the vertical hole 144c, and the like illustrated on the right side of the sensor element 110 in FIG. 3 correspond to the outer inlet 144a located at a position near the downstream side. As the flow rate of measurement-object gas flowing in the second space 122b along the circumferential direction of the inner protective cover 130 increases, the flow rate of measurement-object gas that flows out to the outside from the outer inlet 144a located at such a position near the downstream side tends to increase. When measurement-object gas flows out from the outer inlet 144a to the outside, measurement-object gas that reaches the element chamber inlet 127 reduces accordingly, so the response of specific gas concentration detection decreases. In this way, generally, as the flow rate of measurement-object gas that flows in the second space 122b along the circumferential direction of the inner protective cover 130 increases, the response of specific gas concentration detection is easier to decrease. In contrast, in the gas sensor 100 of the present embodiment, when the cross-sectional area Ds is less than or equal to 6.4 mm$^2$, measurement-object gas is less likely to flow in the second space 122b along the circumferential direction of the inner protective cover 130. Therefore, it is possible to suppress a decrease in response due to flow of measurement-object gas in the second space 122b along the circumferential direction of the inner protective cover 130 as described above. Thus, the gas sensor 100 of the present embodiment is capable of reducing a decrease in response at a low flow speed of measurement-object gas. The cross-sectional area Ds is desirably smaller as described above, and the cross-sectional area Ds may be greater than or equal to 0.5 mm$^2$.

With the gas sensor 100 of the present embodiment described in detail above, since the cross-sectional area Cs is greater than or equal to 14.0 mm$^2$ and the cross-sectional area Ds is less than or equal to 6.4 mm$^2$, it is possible to reduce a decrease in response at a low flow speed of measurement-object gas.

It is desirable that the cross-sectional area Cs be greater than or equal to 20.0 mm$^2$, it is more desirable that the cross-sectional area Cs be greater than or equal to 20.9 mm$^2$, it is further desirable that the cross-sectional area Cs be greater than or equal to 22.9 mm$^2$, it is further more desirable that the cross-sectional area Cs be greater than or equal to 30 mm$^2$, and it is most desirable that the cross-sectional area Cs be greater than or equal to 40 mm$^2$. As the cross-sectional area Cs increases, measurement-object gas tends to move from the outside of the second member 135 toward the inside of the second member 135 in the second space 122b, so an advantageous effect of suppressing a decrease in response at a low flow speed of measurement-object gas is enhanced. In addition, it is desirable that the cross-sectional area Ds be less than or equal to 6.0 mm$^2$, it is more desirable that the cross-sectional area Ds be less than or equal to 5.9 mm$^2$, it is further desirable that the cross-sectional area Ds be less than or equal to 5.0 mm$^2$, and it is further more desirable that the cross-sectional area Ds be less than or equal to 4.0 mm$^2$. As the cross-sectional area Ds reduces, measurement-object gas can be more suppressed to flow in the second space 122b along the circumferential direction of the inner protective cover 130, so an advantageous effect of suppressing a decrease in response at a low flow speed of measurement-object gas is enhanced. The cross-sectional area Cs may be, for example, less than or equal to 73.1 mm$^2$, or may be less than or equal to 70.0 mm$^2$, or may be less than or equal to 60.0 mm$^2$, or may be less than or equal to 57.0 mm$^2$. The cross-sectional area Ds may be, for example, greater than or equal to 1.2 mm$^2$, or may be greater than or equal to 1.5 mm$^2$, or may be greater than or equal to 2.0 mm$^2$.

In addition, it is desirable that a cross-sectional area ratio As/Bs between the cross-sectional area As and the cross-sectional area Bs be greater than or equal to 1.0, and it is more desirable that the cross-sectional area ratio As/Bs be greater than or equal to 1.41 and less than or equal to 4.70. When the cross-sectional area As is too small, measurement-object gas in the first space 122a is difficult to flow into the second space 122b and, as a result, measurement-object gas is difficult to flow into the element chamber inlet 127. When the cross-sectional area Bs is too small, measurement-object gas in the second space 122b is difficult to flow into the element chamber inlet 127. In contrast, when the cross-sectional area ratio As/Bs is greater than or equal to 1.41 and less than or equal to 4.70, the balance in size between the cross-sectional areas As and Bs is good, and measurement-object gas in the first space 122a tends to pass through the second space 122b and flow into the element chamber inlet 127, so it is possible to further suppress a decrease in response at a low flow speed of measurement-object gas.

Furthermore, in the gas sensor 100, the first member 131 and the second member 135 form the element chamber inlet 127 such that the element-side opening 129 is open in the downward direction. Therefore, it is possible to reduce a situation in which measurement-object gas having flowed out from the element-side opening 129 perpendicularly strikes the surface (surface other than the gas inlet port 111) of the sensor element 110 and to reduce a situation in which measurement-object gas passes along the surface of the sensor element 110 over a long distance and then reaches the gas inlet port 111. Thus, it is possible to suppress cooling of the sensor element 110. In addition, cooling of the sensor element 110 is suppressed by adjusting the orientation of the opening of the element-side opening 129, and the flow rate or flow speed of measurement-object gas inside the inner protective cover 130 is not reduced, so a decrease in the response of specific gas concentration detection is also reduced. With these configuration, it is possible to suppress a decrease in the heat retaining property of the sensor element 110 while suppressing a decrease in response.

The present invention is not limited to the above-described embodiment and may be, of course, implemented in various modes within the technical scope of the present invention.

For example, the shape of the protective cover 120 is not limited to the above-described embodiment. The shape of the protective cover 120 or the shape, number, arrangement, and the like of each of the element chamber inlet 127, element chamber outlet 138a, outer inlet 144a, and outer outlet 147a may be changed as needed. For example, the tip end portion 146 of the outer protective cover 140 has a closed-end cylindrical shape and has the side portion 146a, the bottom portion 146b, and the tapered portion 146c.

Alternatively, the tip end portion 146 may have a cylindrical shape without the tapered portion 146c. The tip end portion 138 of the inner protective cover 130 has such a shape that the outside diameter of the side portion 138d is constant and the side portion 138d and the bottom portion 138e have the same diameters. Alternatively, the tip end portion 138 may have such a shape that the outside diameter of the side portion 138d reduces as it approaches the bottom portion 138e, for example, an inverted truncated cone shape. FIG. 8 is a longitudinal sectional view of a gas sensor 200 (which corresponds to the cross-sectional view of the gas sensor 100, taken along the line B-B), in which the tip end portion 146 of the outer protective cover 140 has a cylindrical shape without the tapered portion 146c and the tip end portion 138 of the inner protective cover 130 has an inverted truncated cone shape. FIG. 8 also shows an enlarged view around the second space 122b. FIG. 9 is a cross-sectional view of an outer protective cover 240, taken along the line F-F in FIG. 8. FIG. 10 is a view along the arrow G in FIG. 8. In FIG. 8 to FIG. 10, like reference signs are assigned to the same components as those of the gas sensor 100, and the detailed description thereof is omitted. As shown in FIG. 8, a protective cover 220 of the gas sensor 200 includes an inner protective cover 230 instead of the inner protective cover 130, and includes an outer protective cover 240 instead of the outer protective cover 140. A second member 235 of the inner protective cover 230 has a tip end portion 238 having an inverted truncated cone shape, instead of the tip end portion 138 and the stepped portion 139. The tip end portion 238 has an element chamber outlet 238a that communicates with the sensor element chamber 124 and the second gas chamber 126 and that is an outlet for measurement-object gas from the sensor element chamber 124. The element chamber outlet 238a is a single circular vertical hole formed at the center of the bottom surface of the tip end portion 238. The outer protective cover 240 has a closed-end cylindrical (cylindrical) tip end portion 246 smaller in inside diameter than the body portion 143, instead of the tip end portion 146. The tip end portion 246 has a side portion 246a having a side surface along the central axis direction (up-down direction in FIG. 8) of the outer protective cover 240 and of which the outside diameter is smaller than the inside diameter of the side portion 143a, and a bottom portion 246b that is the bottom portion of the outer protective cover 240. Outer outlets 247a that are outlets for measurement-object gas to the outside are formed at the tip end portion 246. The outer outlets 247a include a plurality of (here, six) vertical holes 247c formed at equal intervals along the circumferential direction of the outer protective cover 240 at the bottom portion 246b of the tip end portion 246 (see FIG. 8, FIG. 9, and FIG. 10). With the thus configured gas sensor 200 as well, when the cross-sectional area Cs is greater than or equal to 14.0 mm$^2$ and the cross-sectional area Ds is less than or equal to 6.4 mm$^2$, similar advantageous effects to those of the above-described embodiment are obtained.

In the above-described embodiment, the element chamber inlet 127 is a cylindrical gap between the first cylinder portion 134 of the first member 131 and the second cylinder portion 136 of the second member 135; however, the configuration is not limited thereto. The element chamber inlet may have any shape as long as the element chamber inlet is a gap between the first member 131 and the second member 135. For example, the element chamber inlet may be a gap inclined at an angle with respect to the up-down direction of FIG. 3 (see also FIG. 12 (described later)). The number of the element chamber inlets 127 is not limited to one and may be multiple (see also FIG. 11 (described later)). The element chamber outlets 138a, the outer inlets 144a, and the outer outlet 147a each are also not limited to a hole and may be a gap between a plurality of members that make up the protective cover 120, and it is sufficient that the number of each is one or more. The outer inlets 144a include the horizontal holes 144b and the vertical holes 144c. Alternatively, the outer inlets 144a may include only any one-type hole. In addition to or instead of the horizontal holes 144b and the vertical holes 144c, an edge hole may be formed at an edge portion at the boundary between the side portion 143a and the stepped portion 143b. For the element chamber outlets 138a and the outer outlet 147a as well, similarly, any one or more types of a horizontal hole, a vertical hole, and an edge hole may be formed. The outer outlets 147a may include a through-hole provided at the tapered portion 146c.

In the above-described embodiment, the protruding portions 136a are formed on the inner peripheral surface of the second cylinder portion 136; however, the configuration is not limited thereto. It is sufficient that a plurality of protruding portions is formed on at least one of the outer peripheral surface of the first cylinder portion 134 and the inner peripheral surface of the second cylinder portion 136 so as to protrude toward the other surface and contact with the other surface. In the above-described embodiment, as shown in FIG. 3 and FIG. 4, the outer peripheral surfaces of portions where the protruding portions 136a are formed in the second cylinder portion 136 are recessed inward; however, the configuration is not limited thereto. Alternatively, the outer peripheral portions do not need to be recessed. The protruding portions 136a are not limited to a semi-spherical shape and may be any shape. The protruding portions 136a do not need to be formed on the outer peripheral surface of the first cylinder portion 134 or on the inner peripheral surface of the second cylinder portion 136.

In the above-described embodiment, the element chamber inlet 127 is a cylindrical gap between the outer peripheral surface of the first cylinder portion 134 and the inner peripheral surface of the second cylinder portion 136; however, the configuration is not limited thereto. For example, a recessed portion (groove) may be formed on at least one of the outer peripheral surface of the first cylinder portion and the inner peripheral surface of the second cylinder portion, and the element chamber inlet may be a gap formed by the recessed portion between the first cylinder portion and the second cylinder portion. FIG. 11 is a cross-sectional view showing an element chamber inlet 327 of a modification. As shown in FIG. 11, the outer peripheral surface of the first cylinder portion 334 and the inner peripheral surface of the second cylinder portion 336 are in contact with each other, and a plurality of (four in FIG. 11) recessed portions 334a is formed at equal intervals on the outer peripheral surface of the first cylinder portion 334. The gap between the recessed portions 334a and the inner peripheral surface of the second cylinder portion 336 is the element chamber inlet 327. When a plurality of (four in FIG. 11) element chamber inlets is present like the element chamber inlets 327, the total of the cross-sectional areas of the element chamber inlets, that is, a total cross-sectional area, is set for the cross-sectional area Bs.

In the above-described embodiment, the element chamber inlet 127 is a flow channel parallel to the rear end-tip end direction of the sensor element 110 (a flow channel parallel to the up-down direction in FIG. 3); however, the configuration is not limited thereto. For example, each element chamber inlet may be a flow channel inclined at an angle with respect to the up-down direction so as to approach the sensor element 110 toward the lower side. FIG. 12 is a longitudinal sectional view of a gas sensor 400 of a modification in this case. FIG. 12 also shows an enlarged view around the second space 122b. In FIG. 12, like reference signs are assigned to the same components as those of the gas sensor 100 or the gas sensor 200, and the detailed description thereof is omitted. As shown in FIG. 12, a protective cover 420 of the gas sensor 400 includes an inner protective cover 430 instead of the inner protective cover 230. The inner protective cover 430 includes a first member 431 and a second member 435. The first member 431, as compared to the first member 131, includes a cylindrical body portion 434a and a cylindrical first cylinder portion 434b that reduces in diameter toward the lower side, instead of the first cylinder portion 134. The first cylinder portion 434b is connected to the body portion 434a at its upper end portion. The second member 435, as compared to the second member 235, includes a cylindrical second cylinder portion 436 that reduces in diameter toward the lower side, instead of the second cylinder portion 136 and the connection portion 137. The second cylinder portion 436 is connected to the tip end portion 238. The outer peripheral surface of the first cylinder portion 434b and the inner peripheral surface of the second cylinder portion 436 are not in contact with each other, and the gap formed therebetween serves as an element chamber inlet 427. The element chamber inlet 427 has an outer opening 428 that is an opening adjacent to the first gas chamber 122 and an element-side opening 429 that is an opening adjacent to the sensor element chamber 124. The element chamber inlet 427 is a flow channel inclined at an angle with respect to the up-down direction so as to approach the sensor element 110 (so as to approach the central axis of the inner protective cover 430) toward the lower side according to the shapes of the first cylinder portion 434b and the second cylinder portion 436. Similarly, the element-side opening 429 is open at an angle with respect to the up-down direction so as to approach the sensor element 110 toward the lower side (see the enlarged view in FIG. 12). When the element chamber inlet 427 is a flow channel inclined at an angle with respect to the up-down direction or when the element-side opening 429 is open at an angle with respect to the up-down direction in this way, the direction of flow of measurement-object gas that flows from the element-side opening 429 to the sensor element chamber 124 is a direction inclined at an angle with respect to the up-down direction. Thus, similar advantageous effects to those of the element chamber inlet 127 or the element-side opening 129 of the above-described embodiment are obtained. In other words, it is possible to reduce a situation in which measurement-object gas perpendicularly strikes the surface (surface other than the gas inlet port 111) of the sensor element 110 and to reduce a situation in which measurement-object gas passes along the surface of the sensor element 110 over a long distance and then reaches the gas inlet port 111. Thus, it is possible to suppress cooling of the sensor element 110. In FIG. 12, the width of the element chamber inlet 427 narrows toward the lower side of the sensor element 110. Therefore, the opening area of the element-side opening 429 is less than the opening area of the outer opening 428. In other words, in the element chamber inlet 427, the distance A4 is less than the distance A5 described with reference to FIG. 7. Thus, when measurement-object gas flows in from the outer opening 428 and flows out from the element-side opening 429, the flow speed of measurement-object gas increases at the time of flowing out as compared to at the time of flowing in. Therefore, it is possible to improve the response of specific gas concentration detection. In this gas sensor 400, the space between the outer protective cover 240 and the second cylinder portion 436 of the second member 435 is the first space 122a. The space above the upper end of the second cylinder portion 436 and between the outer protective cover 240 and the body portion 434a of the first member 431 is the second space 122b. In FIG. 12, the element chamber inlet 427 is a flow channel inclined at an angle with respect to the up-down direction, the element-side opening 429 is open at an angle with respect to the up-down direction, and the opening area of the element-side opening 429 is less than the opening area of the outer opening 428. Alternatively, one or more of these three features may be omitted, or a gas sensor may have one or more of these three features. With the thus configured gas sensor 400 as well, when the cross-sectional area Cs is greater than or equal to 14.0 mm$^2$ and the cross-sectional area Ds is less than or equal to 6.4 mm$^2$, similar advantageous effects to those of the above-described embodiment are obtained. In the gas sensor 400 of FIG. 12, as in the case of the gas sensor 200, the tip end portion 246 of the outer protective cover 240 has a cylindrical shape without a tapered portion, and the tip end portion 238 of the inner protective cover 430 has an inverted truncated cone shape. Alternatively, the gas sensor 400 may have the tip end portion 138, the stepped portion 139, and the tip end portion 146 as in the case of the gas sensor 100.

In the above-described embodiment, the element-side opening 129 is open in the downward direction; however, the configuration is not limited thereto. The element-side opening 129 may be open to the sensor element chamber 124, for example, in a direction perpendicular to the downward direction.

In the above-described embodiment, a surface that defines the upper end of the second space 122b is the lower surface of the stepped portion 133 of the first member 131; however, the configuration is not limited thereto. For example, the lower surface of the housing 102 may be a surface that defines the upper end of the second space 122b.

In the above-described embodiment, the inner protective cover 130 includes two members, that is, the first member 131 and the second member 135. Alternatively, the first member 131 and the second member 135 may be an integrated member.

In the above-described embodiment, the gas inlet port 111 is open at the tip end surface of the sensor element 110 (the lower surface of the sensor element 110 in FIG. 3); however, the configuration is not limited thereto. For example, the gas inlet port 111 may be open at the side surface of the sensor element 110 (the surface, extending in the up-down direction, of the sensor element 110 in FIG. 4).

In the above-described embodiment, the sensor element 110 includes the porous protective layer 110a. Alternatively, the sensor element 110 does not need to include the porous protective layer 110a.

In the above-described embodiment, the protective cover 120 is described as part of the gas sensor 100. Alternatively, the protective cover 120 may be distributed solely.

Although not described in the above-described embodiment, it is desirable that the gas sensor 100 satisfy both the following first condition and second condition. The first condition is a condition in which any of the outer inlet 144a, element chamber outlet 138a, and outer outlet 147a has at least one hole through which a sphere having a diameter of 1.5 mm is able to pass. The second condition is a condition in which the width of a flow channel for measurement-object gas in the protective cover 120 is adjusted so that a sphere having a diameter of 0.8 mm is able to reach the gas inlet port 111 from the outer inlets 144a. The second condition is, in other words, a condition in which the minimum value of a flow channel width (referred to as minimum flow channel width) in a flow channel through which measurement-object gas in an area from the outer inlets 144a to the gas inlet port 111 needs to definitely pass is greater than or equal to 0.8 mm. For example, in the gas sensor 100 of the above-described embodiment, when the distance A6 shown in FIG. 7 is less than any of the distance A4, the distance A5, and the distance A7 shown in FIG. 4 and FIG. 7, the minimum flow channel width becomes a value of the distance A6. In this case, the second condition is satisfied when the distance A6 is greater than or equal to 0.8 mm. Measurement-object gas that flows in the pipe 20 may contain soot, and, when both the first condition and the second condition are satisfied, the soot resistance of the gas sensor 100 improves. For example, when the distance A6 is less than 0.8 mm, soot may clog a gap between the lower end of the first cylinder portion 134 and the connection portion 137. In contrast, when the distance A6 is greater than or equal to 0.8 mm, such clogging of soot is reduced. Such an advantageous effect that the soot resistance improves as a result of fulfillment of the first condition and the second condition is obtained regardless of whether the above-described cross-sectional area Cs is greater than or equal to 14.0 mm$^2$ or whether the cross-sectional area Ds is greater than or equal to 0.5 mm$^2$ and less than or equal to 6.4 mm$^2$. Not limited to the gas sensor 100, even with a gas sensor including a protective cover having any of other shapes of the above-described various modifications and the like, an advantageous effect that the soot resistance improves is obtained when both the first condition and the second condition are satisfied. For example, in the gas sensor 100, when the minimum value of the distance A4, the distance A5, and the distance A7 is smaller than the distance A6 shown in FIG. 7, the minimum flow channel width becomes the minimum value. In this case, when the minimum value is greater than or equal to 0.8 mm (in other words, any of the distance A4, the distance A5, and the distance A7 is greater than or equal to 0.8 mm), the second condition is satisfied. In this case, when the first condition is further satisfied, an advantageous effect that the soot resistance improves is obtained. When the outer inlets 144a include a plurality of holes, it is sufficient that there are one or more holes through which a sphere having a diameter of 1.5 mm is able to pass among the plurality of holes in order to satisfy the first condition, and it is desirable that the number of holes through which a sphere having a diameter of 1.5 mm is able to pass occupy 60% or more of the plurality of holes or the total of the opening areas of holes through which a sphere having a diameter of 1.5 mm is able to pass occupy 60% or more of the total of the opening areas of the plurality of holes. This also similarly applies to the element chamber outlets 138a and the outer outlet 147a. It is desirable that, in addition to the first condition and the second condition, the following third condition be also satisfied. The second condition is a condition in which the width of a flow channel for measurement-object gas in the protective cover 120 is adjusted so that a sphere having a diameter of 0.8 mm is able to reach the outer outlet 147a from the gas inlet port 111.

EXAMPLES

Hereinafter, specific examples of a manufactured gas sensor will be described as examples. Test Examples 2 to 4, 6 to 8, 10 to 12, 14 to 16, 18, and 19 correspond to examples of the present invention, and Test Examples 1, 5, 9, 13, and 17 correspond to comparative examples. The present invention is not limited to the following examples.

Example 1

The gas sensor 200 shown in FIG. 8 to FIG. 10 was assumed as Test Example 1. Specifically, the first member 131 of the inner protective cover 230 was configured such that the sheet thickness was 0.3 mm, the axial length was 10.2 mm, the axial length of the large-diameter portion 132 was 1.8 mm, the outside diameter of the large-diameter portion 132 was 14.4 mm, the axial length of the first cylinder portion 134 was 8.4 mm, the outside diameter of the first cylinder portion 134 was 8.48 mm, and the radius Br2 of the outside diameter of the first cylinder portion 134 was 4.24 mm. The second member 235 was configured such that the sheet thickness was 0.3 mm, the axial length was 11.5 mm, the axial length of the second cylinder portion 136 was 4.941 mm, the inside diameter of the second cylinder portion 136 was 9.7 mm, the radius Ar2 of the outside diameter of the second cylinder portion 136 was 5.15 mm, the radius Br1 of the inside diameter of the second cylinder portion 136 was 4.85 mm, the axial length of the tip end portion 238 was 4.9 mm, and the diameter of the bottom surface of the tip end portion 238 was 3.0 mm. The diameter of the element chamber outlet 238a was set to 1.5 mm. The outer protective cover 240 was configured such that the sheet thickness was 0.4 mm, the axial length was 24.35 mm, the axial length of the large-diameter portion 142 was 5.75 mm, the outside diameter of the large-diameter portion 142 was 15.2 mm, the axial length of the body portion 143 was 9.0 mm (the axial length from the upper end of the body portion 143 to the upper surface of the stepped portion 143b was 8.7 mm), the outside diameter of the body portion 143 was 14.6 mm, the radius Ar1 of the inside diameter of the body portion 143 was 6.9 mm, the axial length of the tip end portion 246 was 9.6 mm, and the outside diameter of the tip end portion 246 was 8.7 mm. The outer inlets 144a were configured such that the six horizontal holes 144b having a diameter of 1.5 mm and the six vertical holes 144c having a diameter of 1 mm were alternately formed at equal intervals (an angle formed between the adjacent holes was 30°). The outer outlets 247a had no horizontal hole, and included the six vertical holes 247c, and the diameter of each vertical hole 247c was set to 1 mm. The material of the protective cover 220 was SUS310S. The sensor element 110 of the gas sensor 200 was configured such that the width (the length in the right-left direction in FIG. 4) was 4 mm and the thickness (the length in the up-down direction in FIG. 4) was 1.5 mm. The porous protective layer 110a was an alumina porous body, and had a thickness of 400 μm. The height C of the second space 122b was set to 3.759 mm, the cross-sectional area As was set to 66.2 mm$^2$, the cross-sectional area Bs was set to 15.9 mm$^2$, the cross-sectional area Cs was set to 114.5 mm$^2$, and the cross-sectional area Ds was set to 10.0 mm$^2$. The cross-sectional area ratio As/Bs was set to 4.2, and the volume V of the second space 122b was set to 349.94 mm$^3$.

Example 2

The same gas sensor 200 as that of Test Example 1 was employed as Test Example 2 except that the height C was set to 2.2 mm by extending the axial length of the second cylinder portion 136 (to 6.5 mm). In Test Example 2, the cross-sectional area As was set to 66.2 mm$^2$, the cross-sectional area Bs was set to 15.9 mm$^2$, the cross-sectional area Cs was set to 67.0 mm$^2$, the cross-sectional area Ds was set to 5.9 mm², the cross-sectional area ratio As/Bs was set to 4.2, and the volume V was set to 204.80 mm³.

Example 3

The gas sensor 100 shown in FIG. 3 to FIG. 7 was assumed as Test Example 3. Specifically, the first member 131 of the inner protective cover 130 was configured such that the sheet thickness was 0.3 mm, the axial length was 10.2 mm, the axial length of the large-diameter portion 132 was 1.8 mm, the outside diameter of the large-diameter portion 132 was 14.4 mm, the axial length of the first cylinder portion 134 was 8.4 mm, the outside diameter of the first cylinder portion 134 was 8.48 mm, and the radius Br2 of the outside diameter of the first cylinder portion 134 was 4.24 mm. The second member 135 was configured such that the sheet thickness was 0.3 mm, the axial length was 15.1 mm, the axial length of the second cylinder portion 136 was 7.326 mm, the inside diameter of the second cylinder portion 136 was 9.7 mm, the radius Ar2 of the outside diameter of the second cylinder portion 136 was 5.15 mm, the radius Br1 of the inside diameter of the second cylinder portion 136 was 4.85 mm, the axial length of the tip end portion 138 was 4.9 mm, and the outside diameter of the side portion 138d of the tip end portion 138 was 5.6 mm. The element chamber outlets 138a were configured such that the four horizontal holes 138b having a diameter of 1.5 mm were formed at equal intervals. The outer protective cover 140 was configured such that the sheet thickness was 0.4 mm, the axial length was 24.35 mm, the axial length of the large-diameter portion 142 was 5.75 mm, the outside diameter of the large-diameter portion 142 was 15.2 mm, the axial length of the body portion 143 was 9.0 mm (the axial length from the upper end of the body portion 143 to the upper surface of the stepped portion 143b was 8.7 mm), the outside diameter of the body portion 143 was 14.6 mm, the radius Ar1 of the inside diameter of the body portion 143 was 6.9 mm, the axial length of the tip end portion 146 was 9.6 mm, the axial length of the side portion 146a of the tip end portion 146 was 6.9 mm, the outside diameter of the tip end portion 146 was 8.7 mm, and the diameter of the bottom portion 146b of the tip end portion 146 was 2.6 mm. The outer inlets 144a were configured such that the six horizontal holes 144b having a diameter of 1.5 mm and the six vertical holes 144c having a diameter of 1.0 mm were alternately formed at equal intervals. The diameter of the outer outlet 147a (vertical hole 147c) was set to 2.0 mm. The material of the protective cover 120 was SUS310S. The sensor element 110 of the gas sensor 100 was configured such that the width (the length in the right-left direction in FIG. 4) was 4 mm and the thickness (the length in the up-down direction in FIG. 4) was 1.5 mm. The porous protective layer 110a was an alumina porous body, and had a thickness of 400 μm. In Test Example 3, the height C was set to 1.374 mm, the cross-sectional area As was set to 66.2 mm², the cross-sectional area Bs was set to 15.9 mm², the cross-sectional area Cs was set to 41.9 mm², the cross-sectional area Ds was set to 3.7 mm², the cross-sectional area ratio As/Bs was set to 4.2, and the volume V was set to 127.91 mm³.

Example 4

The same gas sensor 100 as that of Test Example 3 was employed as Test Example 4 except that the height C was set to 0.685 mm by extending the axial length of the second cylinder portion 136 (to 8.015 mm). In Test Example 4, the cross-sectional area As was set to 66.2 mm², the cross-sectional area Bs was set to 15.9 mm², the cross-sectional area Cs was set to 20.9 mm², the cross-sectional area Ds was set to 1.8 mm², the cross-sectional area ratio As/Bs was set to 4.2, and the volume V was set to 63.77 mm³.

Examples 5 to 8

The same gas sensors as those of Test Examples 1 to 4 were employed as Test Examples 5 to 8 except that the radius Ar2 was set to 5.3 mm and the radius Br1 was set to 5.0 mm by changing the diameter of the second cylinder portion 136.

Examples 9 to 12

The same gas sensors as those of Test Examples 1 to 4 were employed as Test Examples 9 to 12 except that the radius Ar2 was set to 5.45 mm and the radius Br1 was set to 5.15 mm by changing the diameter of the second cylinder portion 136.

Examples 13 to 16

The same gas sensors as those of Test Examples 1 to 4 were employed as Test Examples 13 to 16 except that the radius Ar2 was set to 5.6 mm and the radius Br1 was set to 5.3 mm by changing the diameter of the second cylinder portion 136.

Examples 17 to 19

The same gas sensors as those of Test Examples 1 to 3 were employed as Test Examples 17 to 19 except that the radius Ar2 was set to 5.75 mm and the radius Br1 was set to 5.45 mm by changing the diameter of the second cylinder portion 136.

[Evaluation of Response and Heat Retaining Property]

The gas sensors of Test Examples 1 to 19 each were connected to a pipe similarly as shown in FIG. 1 and FIG. 2. Gas obtained by adjusting the atmosphere by mixture of oxygen into a selected oxygen concentration was used as measurement-object gas, and the measurement-object gas was caused to flow in the pipe at a flow speed of 0.73 m/s. Then, a temporal change in the output of the sensor element in the case where the oxygen concentration of measurement-object gas to be caused to flow in the pipe was changed from 23.6% to 20.9% was investigated. Where the output value of the sensor element just before the oxygen concentration was changed was 0% and the output value at the time when the output of the sensor element after a change of the oxygen concentration varied and then became stable was 100%, an elapsed time from when the output value exceeds 10% to when the output value exceeds 90% was defined as a response time [sec] of specific gas concentration detection. It means that the response of specific gas concentration detection increases as the response time shortens. Measurement of a response time was performed multiple times for each test example, and the average of each was determined as a response time for an associated test example. In each of Test Examples 1 to 19, a response time was similarly measured when the flow speed of measurement-object gas was set to 1 m/s. In each of Test Examples 1 to 4, a response time was similarly measured when the flow speed of measurement-object gas was set to 2 m/s and also set to 4 m/s. In Test Examples 1 and 2, a response time was similarly measured when the flow speed of measurement-object gas was set to 8 m/s.

Table 1 shows the radii Ar1, Ar2, Br1, Br2, the height C, the cross-sectional areas As to Ds, the cross-sectional area ratio As/Bs, the volume V, the response time, and the evaluation result of the response of each of the gas sensors of Test Examples 1 to 19. In Table 1, the response time when the flow speed of measurement-object gas was set to 1 m/s was used to evaluate the response, and it was determined that the response was excellent (A) when the response time was shorter than or equal to two and half seconds, the response was good (B) when the response time was shorter than or equal to three seconds, and the response was not good (F) when the response time was longer than three seconds. FIG. 13 is a graph showing the relationship between a flow speed and a response time in each of Test Examples 1 to 4. FIG. 14 is a graph showing the relationship between a height C and a response time at a flow speed of 1 m/s in each of Test Examples 1 to 4. FIG. 14 also shows an approximate curve (approximation using a cubic polynomial) showing the relationship between a height C and a response time. A height C at which the response time was three seconds and a height C at which the response time was two and half seconds were calculated based on the approximate curve, and the approximate curve is also shown in FIG. 14. In each of Test Examples 1 to 4, the cross-sectional areas Cs, Ds, and the volume V were changed by changing only the height C, so each of the cross-sectional areas Cs, Ds, and the volume V is a value proportional to the height C. In other words, the relationship between a response time and each of the cross-sectional areas Cs, Ds, and the volume V is also the same except that the graph of FIG. 14 and values on the abscissa axis are different. FIG. 14 also shows the values of the cross-sectional areas Cs, Ds, and the volume V when the response time is three seconds and the values of the cross-sectional areas Cs, Ds, and the volume V when the response time is two and half seconds.

decrease in flow speed. In addition, there is almost no difference in response time among Test Examples 1 to 4 when the flow speed is higher than or equal to 2 m/s; however, there is a large difference in response time among Test Examples 1 to 4 when the flow speed is lower than 2 m/s. As shown in Table 1 and FIG. 13, the response time was shorter in Test Examples 2 to 4 than Test Example 1 and, particularly, the response time of Test Example 3 was the shortest. As is apparent from the approximate curve of FIG. 14, it is found that the response time extends even when the value of any of the height C, the cross-sectional area Cs, the cross-sectional area Ds, and the volume V is too large or too small. The reason why the response time extends when the height C, the cross-sectional area Cs, the cross-sectional area Ds, or the volume V is too small is presumably because particularly the cross-sectional area Cs is too small among these values. In other words, as described above, it is presumable that, when the cross-sectional area Cs is too small, measurement-object gas is less likely to move from the outside of the second member to the inside of the second member in the second space 122b (measurement-object gas is less likely to move toward the inner side in the radial direction of the protective cover) and, as a result, the response is decreased. The reason why the response time extends when the height C, the cross-sectional area Cs, the cross-sectional area Ds, or the volume V is too large is presumably because particularly the cross-sectional area Ds is too large among these values. In other words, as described above, it is presumable that, when the cross-sectional area Ds is too large, measurement-object gas tends to move in the second space 122b along the circumferential direction of the inner protective cover and, as a result, the response is decreased. From the relationship between the approximate curve and a response time in FIG. 14, it is presumable that, when the cross-sectional area Cs is greater than or equal to

| | Radii [mm] | | | | Height C | Cross-sectional area [mm$^2$] | | | | Cross-sectional area ratio | Volume V | Response time [s] | | | | | Evaluation of the response |
|---|---|---|---|---|---|---|---|---|---|---|---|---|---|---|---|---|---|
| | | | | | | | | | | | | Flow speed 0.73 | Flow speed 1 | Flow speed 2 | Flow speed 4 | Flow speed 8 | |
| | Ar1 | Ar2 | Br1 | Br2 | [mm] | As | Bs | Cs | Ds | As/Bs | [mm$^3$] | m/s | m/s | m/s | m/s | m/s | |
| Example 1 | 6.9 | 5.15 | 4.85 | 4.24 | 3.759 | 66.2 | 15.9 | 114.5 | 10.0 | 4.2 | 349.94 | 7.16 | 3.86 | 0.39 | 0.18 | 0.17 | F |
| Example 2 | 6.9 | 5.15 | 4.85 | 4.24 | 2.2 | 66.2 | 15.9 | 67.0 | 5.9 | 4.2 | 204.80 | 5.4 | 2.81 | 0.45 | 0.21 | 0.12 | B |
| Example 3 | 6.9 | 5.15 | 4.85 | 4.24 | 1.374 | 66.2 | 15.9 | 41.9 | 3.7 | 4.2 | 127.91 | 5.04 | 2.21 | 0.39 | 0.15 | — | A |
| Example 4 | 6.9 | 5.15 | 4.85 | 4.24 | 0.685 | 66.2 | 15.9 | 20.9 | 1.8 | 4.2 | 63.77 | 5.64 | 2.6 | 0.45 | 0.18 | — | B |
| Example 5 | 6.9 | 5.3 | 5 | 4.24 | 3.759 | 61.3 | 19.7 | 118.1 | 10.0 | 3.1 | 349.94 | 6.5 | 3.2 | — | — | — | F |
| Example 6 | 6.9 | 5.3 | 5 | 4.24 | 2.2 | 61.3 | 19.7 | 69.1 | 5.9 | 3.1 | 204.80 | 4.6 | 2 | — | — | — | A |
| Example 7 | 6.9 | 5.3 | 5 | 4.24 | 1.374 | 61.3 | 19.7 | 43.2 | 3.7 | 3.1 | 127.91 | 4.4 | 1.9 | — | — | — | A |
| Example 8 | 6.9 | 5.3 | 5 | 4.24 | 0.685 | 61.3 | 19.7 | 21.5 | 1.8 | 3.1 | 63.77 | 5.2 | 2.4 | — | — | — | A |
| Example 9 | 6.9 | 5.45 | 5.15 | 4.24 | 3.759 | 56.3 | 23.5 | 121.6 | 10.0 | 2.4 | 349.94 | 6 | 3 | — | — | — | F |
| Example 10 | 6.9 | 5.45 | 5.15 | 4.24 | 2.2 | 56.3 | 23.5 | 71.2 | 5.9 | 2.4 | 204.80 | 4.3 | 1.85 | — | — | — | A |
| Example 11 | 6.9 | 5.45 | 5.15 | 4.24 | 1.374 | 56.3 | 23.5 | 44.5 | 3.7 | 2.4 | 127.91 | 4.2 | 1.8 | — | — | — | A |
| Example 12 | 6.9 | 5.45 | 5.15 | 4.24 | 0.685 | 56.3 | 23.5 | 22.2 | 1.8 | 2.4 | 63.77 | 5.3 | 2.3 | — | — | — | A |
| Example 13 | 6.9 | 5.6 | 5.3 | 4.24 | 3.759 | 51.1 | 27.2 | 125.2 | 10.0 | 1.9 | 349.94 | 6.3 | 3.3 | — | — | — | F |
| Example 14 | 6.9 | 5.6 | 5.3 | 4.24 | 2.2 | 51.1 | 27.2 | 73.3 | 5.9 | 1.9 | 204.80 | 4.5 | 1.8 | — | — | — | A |
| Example 15 | 6.9 | 5.6 | 5.3 | 4.24 | 1.374 | 51.1 | 27.2 | 45.8 | 3.7 | 1.9 | 127.91 | 4.4 | 2 | — | — | — | A |
| Example 16 | 6.9 | 5.6 | 5.3 | 4.24 | 0.685 | 51.1 | 27.2 | 22.8 | 1.8 | 1.9 | 63.77 | 5.5 | 2.6 | — | — | — | B |
| Example 17 | 6.9 | 5.75 | 5.45 | 4.24 | 3.759 | 45.7 | 30.9 | 128.7 | 10.0 | 1.5 | 349.94 | 7.4 | 3.5 | — | — | — | F |
| Example 18 | 6.9 | 5.75 | 5.45 | 4.24 | 2.2 | 45.7 | 30.9 | 75.3 | 5.9 | 1.5 | 204.80 | 5.6 | 2.4 | — | — | — | A |
| Example 19 | 6.9 | 5.75 | 5.45 | 4.24 | 1.374 | 45.7 | 30.9 | 47.1 | 3.7 | 1.5 | 127.91 | 5.4 | 2.4 | — | — | — | A |

※Radius Ar1 = (Inside diameter of the side portion of the outer protective cover)/2
※Radius Ar2 = (Outside diameter of the second cylinder portion)/2
※Radius Br1 = (Inside diameter of the second cylinder portion)/2
※Radius Br2 = (outside diameter of the first cylinder portion)/2

As shown in Table 1 and FIG. 13, it was found that, in any of Test Examples 1 to 4, the response time had a tendency to extend (the response had a tendency to decrease) with a 14.0 mm$^2$ and the cross-sectional area Ds is less than or equal to 6.4 mm$^2$, the response time at a flow speed of 1 m/s becomes shorter than or equal to three seconds and, as a result, it is possible to reduce a decrease in response at a low flow speed of measurement-object gas. It is also presumable that, when the cross-sectional area Cs is greater than or equal to 22.9 mm² and the cross-sectional area Ds is less than or equal to 5.0 mm², the response time at a flow speed of 1 m/s becomes shorter than or equal to two and half seconds and, as a result, it is possible to further reduce a decrease in response at a low flow speed of measurement-object gas.

As is also shown in FIG. 14, the numeric range of the height C, associated with the state where the cross-sectional area Cs was greater than or equal to 14.0 mm² and the cross-sectional area Ds was less than or equal to 6.4 mm², was greater than or equal to 0.46 mm and less than or equal to 2.40 mm, and the associated numeric range of the volume V was greater than or equal to 43 mm³ and less than or equal to 223 mm³. The numeric range of the height C, associated with the state where the cross-sectional area Cs was greater than or equal to 22.9 mm² and the cross-sectional area Ds was less than or equal to 5.0 mm², was greater than or equal to 0.75 mm and less than or equal to 1.87 mm, and the associated numeric range of the volume V was greater than or equal to 70 mm³ and less than or equal to 174 mm³.

For Test Examples 5 to 19, as well as Test Examples 1 to 4, it was observed that the response time had a tendency to extend (the response had a tendency to decrease) with a decrease in flow speed. For Test Examples 5 to 19 as well, a similar tendency to those of Test Examples 1 to 4 was found between the values of the cross-sectional area Cs and the cross-sectional area Ds and response at a low flow speed. For example, in Test Examples 6 to 8, 10 to 12, 14 to 16, 18, and 19, in which the cross-sectional area Cs was greater than or equal to 14.0 mm² and the cross-sectional area Ds was less than or equal to 6.4 mm², the response time at a flow speed of 1 m/s was shorter than or equal to three seconds (evaluation of response was higher than or equal to "B"). When Test Examples 5 to 8 in which the values of the cross-sectional area As are the same and the values of the cross-sectional area Bs are the same were compared with one another, the response time was the shortest in Test Example 7 that satisfied the condition in which the cross-sectional area Cs was greater than or equal to 22.9 mm² and the cross-sectional area Ds was less than or equal to 5.0 mm². Similarly, when Test Examples 9 to 12 were compared with one another, the response time was the shortest in Test Example 11 that satisfied the condition in which the cross-sectional area Cs was greater than or equal to 22.9 mm² and the cross-sectional area Ds was less than or equal to 5.0 mm². When Test Examples 13 to 16 were compared with one another, the response time was the shortest at a flow speed of 0.73 m/s in Test Example 15 that satisfied the condition in which the cross-sectional area Cs was greater than or equal to 22.9 mm² and the cross-sectional area Ds was less than or equal to 5.0 mm². The response time at a flow speed of 1 m/s was shorter in Test Example 14 than Test Example 15; however, the difference was slight and was presumably regarded as an error. When Test Examples 17 to 19 were compared with one another, the response time was the same at a flow speed of 1 m/s in Test Example 18 and Test Example 19 that satisfied the condition in which the cross-sectional area Cs was greater than or equal to 22.9 mm² and the cross-sectional area Ds was less than or equal to 5.0 mm²; however, the response time at a flow speed of 0.73 m/s was the shortest in Test Example 19 among Test Examples 17 to 19. Therefore, as a whole, it was found that the response time was the shortest in Test Example 19 among Test Examples 17 to 19.

It is assumed that, among Test Examples 2 to 4, 6 to 8, 10 to 12, 14 to 16, 18, and 19 in which the cross-sectional area Cs is greater than or equal to 14.0 mm² and the cross-sectional area Ds is less than or equal to 6.4 mm², Test Examples 2 to 4 in which the cross-sectional area As is the same and the cross-sectional area ratio As/Bs is the same belong to a first group, similarly, Test Examples 6 to 8 belong to a second group, Test Examples 10 to 12 belong to a third group, Test Examples 14 to 16 belong to a fourth group, and Test Examples 18 and 19 belong to a fifth group. When the first to fifth groups are compared with one another, it is found that the response time at a low flow speed tends to be shorter in the first to fourth groups in which the cross-sectional area As falls within the range greater than or equal to 47.3 mm² and less than or equal to 68.1 mm² than the fifth group in which the cross-sectional area As falls outside the range. Therefore, it is presumable that the cross-sectional area As is desirably greater than or equal to 47.3 mm² and less than or equal to 68.1 mm². However, in the fifth group as well, evaluation of response is "A", and an advantageous effect of reducing a decrease in response at a low flow speed of measurement-object gas is obtained.

What is claimed is:

1. A gas sensor comprising:
    a sensor element having a gas inlet port that introduces measurement-object gas and capable of detecting a specific gas concentration of the measurement-object gas having flowed in from the gas inlet port;
    a cylindrical inner protective cover having inside a sensor element chamber in which a tip end of the sensor element and the gas inlet port are disposed, and having one or more element chamber inlets that are inlets to the sensor element chamber and one or more element chamber outlets that are outlets from the sensor element chamber; and
    a cylindrical outer protective cover disposed outside the inner protective cover and having one or more outer inlets that are inlets for the measurement-object gas from an outside and one or more outer outlets that are outlets for the measurement-object gas to the outside, wherein
    the outer protective cover and the inner protective cover form, as spaces between the outer protective cover and the inner protective cover, a first gas chamber that functions as a flow channel for the measurement-object gas between the one or more outer inlets and the one or more element chamber inlets and a second gas chamber that functions as a flow channel for the measurement-object gas between the one or more outer outlets and the one or more element chamber outlets and that does not directly communicate with the first gas chamber,
    the inner protective cover has a cylindrical first member surrounding the sensor element, and a cylindrical second member surrounding the first member,
    the first member and the second member form the one or more element chamber inlets as a gap between the first member and the second member,
    where a direction parallel to an axial direction of the inner protective cover from the tip end of the sensor element toward a rear end of the sensor element is an upward direction and a direction from the rear end of the sensor element toward the tip end of the sensor element is a downward direction, the first gas chamber has a first space that is a space between the outer protective cover and the second member and that functions as a flow channel for the measurement-object gas from the one or more outer inlets in the upward direction and a second space that is a space above an upper end of the second member and between the outer protective cover and the first member and that functions as a flow channel for the measurement-object gas from the first space to the one or more element chamber inlets, a cross-sectional area Cs that is a flow channel cross-sectional area in the second space when the measurement-object gas passes from an outside of the second member toward an inside of the second member just above the second member is greater than or equal to 14.0 mm$^2$, and a cross-sectional area Ds that is a cross-sectional area perpendicular to a circumferential direction of the inner protective cover in the second space is greater than or equal to 0.5 mm$^2$ and less than or equal to 6.4 mm$^2$.

2. The gas sensor according to claim 1, wherein the cross-sectional area Cs is greater than or equal to 22.9 mm$^2$.

3. The gas sensor according to claim 1, wherein the cross-sectional area Ds is less than or equal to 5.0 mm$^2$.

4. The gas sensor according to of claim 1, wherein a cross-sectional area ratio As/Bs between a cross-sectional area As of a second space inlet that is an inflow port for the measurement-object gas from the first space to the second space and a cross-sectional area Bs that is a total cross-sectional area of the one or more element chamber inlets is greater than or equal to 1.41 and less than or equal to 4.70.

5. The gas sensor according to claim 1, wherein a cross-sectional area As of a second space inlet that is an inflow port for the measurement-object gas from the first space to the second space is greater than or equal to 47.3 mm$^2$ and less than or equal to 68.1 mm$^2$.

6. The gas sensor according to claim 1, wherein a cross-sectional area Bs that is a total cross-sectional area of the one or more element chamber inlets is greater than or equal to 14.5 mm$^2$ and less than or equal to 33.4 mm$^2$.

7. The gas sensor according to claim 1, wherein the first member and the second member form the one or more element chamber inlets such that an element-side opening that is an opening adjacent to the sensor element chamber of each of the one or more element chamber inlets is open in the downward direction.

8. The gas sensor according to claim 1, wherein the first member has a first cylinder portion surrounding the sensor element, the second member has a second cylinder portion larger in diameter than the first cylinder portion, and the one or more element chamber inlets are a cylindrical gap between an outer peripheral surface of the first cylinder portion and an inner peripheral surface of the second cylinder portion.

9. A protective cover for protecting a sensor element having a gas inlet port that introduces measurement-object gas and capable of detecting a specific gas concentration of the measurement-object gas that has flowed in from the gas inlet port, the protective cover comprising:

a cylindrical inner protective cover having inside a sensor element chamber for disposing a tip end of the sensor element and the gas inlet port inside, and having one or more element chamber inlets that are inlets to the sensor element chamber and one or more element chamber outlets that are outlets from the sensor element chamber; and a cylindrical outer protective cover disposed outside the inner protective cover and having one or more outer inlets that are inlets for the measurement-object gas from an outside and one or more outer outlets that are outlets for the measurement-object gas to the outside, wherein the outer protective cover and the inner protective cover form, as spaces between the outer protective cover and the inner protective cover, a first gas chamber that functions as a flow channel for the measurement-object gas between the one or more outer inlets and the one or more element chamber inlets and a second gas chamber that functions as a flow channel for the measurement-object gas between the one or more outer outlets and the one or more element chamber outlets and that does not directly communicate with the first gas chamber, the inner protective cover includes a cylindrical first member and a cylindrical second member surrounding the first member, the first member and the second member form the one or more element chamber inlets as a gap between the first member and the second member, where a direction parallel to an axial direction of the inner protective cover from a bottom portion of the outer protective cover toward a side opposite from the bottom portion is an upward direction and a direction from the side opposite from the bottom portion of the outer protective cover toward the bottom portion is a downward direction, the first gas chamber has a first space that is a space between the outer protective cover and the second member and that functions as a flow channel for the measurement-object gas from the one or more outer inlets in the upward direction and a second space that is a space above an upper end of the second member and between the outer protective cover and the first member and that functions as a flow channel for the measurement-object gas from the first space to the one or more element chamber inlets, a cross-sectional area Cs that is a flow channel cross-sectional area in the second space when the measurement-object gas passes from an outside of the second member toward an inside of the second member just above the second member is greater than or equal to 14.0 mm$^2$, and a cross-sectional area Ds that is a cross-sectional area perpendicular to a circumferential direction of the inner protective cover in the second space is greater than or equal to 0.5 mm$^2$ and less than or equal to 6.4 mm$^2$.

* * * * *